US006235496B1

(12) United States Patent
Yu

(10) Patent No.: US 6,235,496 B1
(45) Date of Patent: May 22, 2001

(54) NUCLEIC ACID ENCODING MAMMALIAN MU OPIOID RECEPTOR

(75) Inventor: Lei Yu, Indianapolis, IN (US)

(73) Assignee: Advanced Research & Technology Institute, Indianapolis, IN (US)

( * ) Notice: Subject to any disclaimer, the term of this patent is extended or adjusted under 35 U.S.C. 154(b) by 0 days.

(21) Appl. No.: 08/120,601

(22) Filed: Sep. 13, 1993

Related U.S. Application Data

(63) Continuation-in-part of application No. 08/056,886, filed on Mar. 8, 1993, now abandoned.

(51) Int. Cl.[7] ............................ C12P 21/06; C12P 21/04; C07H 21/04; C12N 1/20

(52) U.S. Cl. .................. 435/69.1; 435/240.1; 435/320.1; 536/23.1

(58) Field of Search ......................... 536/23.1; 435/69.1, 435/240.1, 320.1

(56) References Cited

FOREIGN PATENT DOCUMENTS

9404552 * 3/1994 (WO) .

OTHER PUBLICATIONS

Chen et al., Mol. Pharm., v. 44, p. 8, 1993.*
Fukuda et al., FEBS, v. 327, p. 311, 1993.*
Li et al., PNAS, v. 88, p. 7739, 1991.*
Loh et al., Annu. Rev. Toxicol., v. 30, p. 123, 1990.*
Maneckjee et al., J. Neuroimmunol., v. 17, p. 199, 1988.*
Mirendorf et al., Methods in Enz., v. 152, p. 458, 1987 Academic Press.*
Sambrook et al., Molecular Cloning, v. 3, chp. 16, 1989 CSH Press.*
Schofield et al., Embo J., v. 8, p. 489, 1989.*
Veda et al., PNAS, vol. 85, pp. 7013–7017, 1988.*
Lin et al., Science, vol. 254, pp. 1022–1024, 1991.*
Dohlman et al., "Model Systems for the Study of Seven–Transmembrane–Segment Receptors," *Annu. Rev. Biochem.*, 60:653–688, 1991.
Dohlman et al., "A Family of Receptors Coupled to Guanine Nucleotide Regulatory Proteins," *Biochemistry*, 26:2657–2664, 1987.
Evans et al., "Cloning of a Deltas Opioid Receptor by Functional Expression," *Science*, 258:1952–1954, 1992.
Frielle et al., "Structural Basis of β–adrenergic Receptor Subtype Specificity Studied with Chimeric β1/β2–adrenergic Receptors," *Proc. Natl. Acad. Sci. USA*, 85:9494–9498, 1988.
Gioannini, T.L. et al., "Evidence for the Presence of Disulfide Bridges in Opioid Receptors Essential for Ligand Binding. Possible Role in Receptor Activation," *J. Mol. Recogn.*, 2:44–48, 1989.

Kieffer et al., "The δ–opioid Receptor: Isolation of a cDNA by Expression Cloning and Pharmacological Characterization," *Proc. Natl. Acad. Sci. USA*, 89:12048–12052, 1992.
Lutz et al., "Opioid Receptors and Their Pharmacological Profiles," *J. Receptor Res.*, 12:267–286, 1992.
Mansour et al., "Anatomy of CNS Opioid Receptors," *Trends in Neurosci.*, 7:2445–2453, 1987.
Nock et al., "Autoradiography of [3H] U–69593 Binding Sites in Rat Brain: Evidence for K Opioid Receptor Subtypes," *Eur. J. Pharmacol.*, 154:27–34, 1988.
Simon, "Opioid Receptors and Endogenous Opioid Peptides," *Medicinal Res. Rev.*, 11:357–374, 1991.
Unterwald et al., "Neuroanatomical Localization of K1 and K2 Opioid Receptors in Rat and Guinea Pig Brain," *Brain Res.*, 562:57–65, 1991.
Xie et al., "Expression Cloning of cDNA Encoding a Seven–helix Receptor from Human Placenta with Affinity for Opioid Ligands," *Proc. Natl. Acad. Sci. USA*, 89:4124–4128, 1992.
Yamada et al., "Cloning and Functional Characterization of a Family of Human and Mouse Somatostatin Receptors Expressed in Brain, Gastrointestinal Tract, and Kidney," *Proc. Natl. Acad. Sci. USA*, 89:251–255, 1992.
Yasuda et al., "Cloning of a Novel Somatostatin Receptor, SSTR3, Coupled to Adenylylcyclase," *J. Biol. Chem.*, 267:20422–20428, 1992.
Probst et al., "Sequence Alignment of the G–Protein Coupled Receptor Superfamily," *DNA and Cell Biology*, 11:1–20, 1992.
Chen et al., Mol. Pharm., vol. 44, p.8, 1993.*
Fukada et al., FEBS, Vol. 327, p. 311, 1993.*
Li et al., PNAS, Vol. 88, P. 7739, 1991.*
Loh et al., Annu. Rev. Toxicol., vol. 30, p. 123, 1990.*
Maneckjee et al., J. Neuroimmunol., vol. 17, p. 199, 1988.*
Mirendorf et al., Methods in Enz., vol. 152, p. 458, 1987 Academic Press.*
Sambrook et al., Molecular Cloning, vol. 3, chp. 16, 1989 CSH Press.*
Schofield et al., Embo J., vol. 8, p. 489, 1989.*

* cited by examiner

*Primary Examiner*—Gary L. Kunz
*Assistant Examiner*—Robert S. Landsman
(74) *Attorney, Agent, or Firm*—Fulbright & Jaworski LLP

(57) ABSTRACT

The invention relates generally to compositions of and methods for obtaining mu opioid receptor polypeptides. The invention relates as well to polynucleotides encoding mu opioid receptor polypeptides, the recombinant vectors carrying those sequences, the recombinant host cells including either the sequences or vectors, and recombinant opioid receptor polypeptides. The invention includes as well, methods for using the isolated, recombinant receptor polypeptide in assays designed to select and improve substances capable of interacting with mu opioid receptor polypeptides for use in diagnostic, drug design and therapeutic applications.

15 Claims, 5 Drawing Sheets

```
Rat MOR-1                                                                                          30  SEQ ID NO:2
Mouse DOR-1     MDSSTGPGNTSDCSDPLAQASCSPAPGSWL                                                     11  SEQ ID NO:7
Rat Somatostatin Receptor 1          MELV-SARAE-                                                   20  SEQ ID NO:8
Rat Somatostatin Receptor 2     MFPNGTAPSPTS--SSSPGG                                                5  SEQ ID NO:9
                                              MELTS MOR   NLSHVDGNQSDPCGLNRTGLGGNDLSCPQTGSPSMVT AITIMALYSIVC       79
DOR   QS-PLV -L--AFPSAFPSAGA-A-GS-GAR-A--LAL---A-T----A--      60
SOM1  CGEGLCSRGPGSGAADGMEEPGRN-SQNGTL-EGQGS  --L-SFI--V--      69
SOM2  EQFNGSQVWIPSPFDLNGS--PSNGSNQTEPYD-TSN--VL TFI-FV---      54
                                       *
MOR   VVGLFGNFLVMYVIVRYTKMKTATNIYIFNLALADALATSTLPFQSVNYL      129
DOR   A-----L--V----FG------L-------------------------        110
SOM1  L-----C---SM-I---A-----------L-----I---E-LMLSV--LVTST-  119
SOM2  -----C--T--I---A-----I-------L---I---E-FMLG---LAMQVA    104
          =                               II
MOR   MGTWPFGTILCKIVISIDYYNMFTSIFTLCT MSVDRYIAVCHPVKALDF      178
DOR   -E-------EL----A-L---------M---                         159
SOM1  LRH-----AL--RL-L-V-A-----YC---VL----V--V---I--ARY       168
SOM2  LVH----KAI-RV-MTV-GI-Q----C--V---I----L--V--I-SAKW      153
              III                                =
MOR   RTPRNAKIVNVCNWILSSAIGLPVMFMATTKYRQGSID CTLTFSHPTWY      227
DOR   ---AK--LI-I-I-V-ASGV-V-I-V--V-QP-D-AVV --M-Q-PS-S--     208
SOM1  -R-TV--V--LGV-V--LLVI--IVVFSR-AANSDGTVA-NMLMPE-AQR      218
SOM2  -R---T--MI--AV-GV-LLVI---I--IY-GLRSN-WGRSS-TINWPGESGA   203
          O                               IV
```

FIG. 1A

```
MOR   WENLLKICVFIFAFIMPILIITVCYGLMILRLKSVRMLSGSKEKDRNLRR        277
DOR   -DTVT-------VV--------L---R--L----S---                    258
SOM1  -LVGFVLYT-LMG-LL-VGA-CL--V-I-AKMRM-ALKA-WQQRK-SE-K         268
SOM2  -YTGFI-YA--LG-LV-LT--CL--LRI-IKV--SGIRV--SKRKKSEKK         253
                    V

MOR   ITRMVLVVVAVFIVCWTPIHIYVIIKALITIPETTFQTV SWHFCIALGY         326
DOR   ------GA-V---A----F--VWT-VD-NRRDPLV-AAL-L-----             308
SOM1  --L--MM--M--VI--M-   FYVV Q-VNVFAEQDDATV-QLSV-             313
SOM2  V----SI-----F--L-FY-FNVSSVSVA-SP-PALKGMFDFVV--T-           302
                         VI           ▶

MOR   TNSCLNPVLYAFLDENFKRCFREFCIPTSSTIEQQNSTRVRQ NTREHPS         375
DOR   A--S-----------------QL-RTPCGRQ-PGSLR-P--AT--RV           357
SOM1  A---A--I--G--SD----S-QRILCLSWMDNAAEEPVDYY ATALKSRA         362
SOM2  A--A--I--A--SD---KS-QNVLCLVKVSGAEDGERSDSKQDKSRLNE          352
                       VII

MOR   TANTVDRTNHQLENLEAETAPLP                                   398
DOR   --C-PSDGPGGGAAA                                           372
SOM1  YSVEDFQPENLESGGVFRNGTCASRISTL                             391
SOM2  -TE- Q--LLNGDLQTSI                                        369
```

*FIG. 1B*

NUCLEIC ACID ENCODING MAMMALIAN MU OPIOID RECEPTOR

The present application is a continuation-in-part of U.S. patent application Ser. No. 08/056,886, filed Mar. 8, 1993, now abandoned.

FIELD OF THE INVENTION

This invention relates generally to compositions of and methods for obtaining mu opioid receptors. The invention relates as well to the DNA sequences encoding mu opioid receptors, the recombinant vectors carrying those sequences, the recombinant host cells including either the sequences or vectors, and recombinant mu opioid receptor polypeptides. The invention includes as well methods for using the isolated, recombinant receptor polypeptides in assays designed to select and improve among candidate substances such as agonists and antagonists of mu opioid receptors and polypeptides for use in diagnostic, drug design and therapeutic applications.

BACKGROUND OF THE INVENTION

Opioid drugs have various effects on perception of pain, consciousness, motor control, mood, and autonomic function and can also induce physical dependence (Koob et al., 1992). The endogenous opioid system plays an important role in modulating endocrine, cardiovascular, respiratory, gastrointestinal and immune functions (Olson et al., 1989). Opioids exert their actions by binding to specific membrane-associated receptors located throughout the central and peripheral nervous system (Pert et al., 1973). The endogenous ligands of these opioid receptors have been identified as a family of more than 20 opioid peptides that derive from the three precursor proteins proopiomelanocortin, proenkephalin, and prodynorphin (Hughes et al., 1975; Akil et al., 1984). Although the opioid peptides belong to a class of molecules distinct from the opioid alkaloids, they share common structural features including a positive charge juxtaposed with an aromatic ring that is required for interaction with the receptor (Bradbury et al., 1976).

Pharmacological studies have suggested that there are numerous classes of opioid receptors, including those designated δ, κ, and μ (Simon, 1991; Lutz et al., 1992). The classes differ in their affinity for various opioid ligands and in their cellular distribution. The different classes of opioid receptors are believed to serve different physiological functions (Olson et al., 1989; Simon, 1991; Lutz and Pfister, 1992). However, there is substantial overlap of function as well as of distribution. Biochemical characterization of opioid receptors from many groups reports a molecular mass of ≈60,000 Da for all three subtypes, suggesting that they could be related molecules (Loh et al., 1990). Moreover, the similarity between the three receptor subtypes is supported by the isolation of (i) anti-idiotypic monoclonal antibodies competing with both μ and δ ligands but not competing with κ ligands (Gramsch et al., 1988; Coscia et al., 1991) and (ii) a monoclonal antibody raised against the purified μ receptor that interacts with both μ and κ receptors (Bero et al., 1988).

Morphine interacts principally with μ receptors and peripheral administration of this opioid induces release of enkephalins (Bertolucci et al., 1992). The δ receptors bind with the greatest affinity to enkephalins and have a more discrete distribution in the brain than either μ or κ receptors, with high concentrations in the basal ganglia and limbic regions. Thus, enkephalins may mediate part of the physiological response to morphine, presumably by interacting with δ receptors. Despite pharmacological and physiological heterogeneity, at least some types of opioid receptors inhibit adenylate cyclase, increase $K^+$ conductance, and inactivate $Ca^{2+}$ channels through a pertussis toxin-sensitive mechanism (Puttfarcken et al., 1988; Attali et al., 1989; Hsia et al., 1984). These results and others suggest that opioid receptors belong to the large family of cell surface receptors that signal through G proteins (Di Chiara et al., 1992; Loh et al., 1990).

Several attempts to clone cDNAs encoding opioid receptors have been reported. A cDNA encoding an opioid-binding protein (OBCAM) with μ selectivity was isolated (Schofield et al., 1989), but the predicted protein lacks transmembrane domains, presumed necessary for signal transduction. More recently, the isolation of another cDNA was reported, which was obtained by expression cloning (Xie et al., 1992). The deduced protein sequence displays seven putative transmembrane domains and is very similar to the human neuromedin K receptor. However, the affinity of opioid ligands for this receptor expressed in COS cells is two orders of magnitude below the expected value, and no subtype selectivity can be shown Many cell surface receptor/transmembrane systems consist of at least three membrane-bound polypeptide components: (a) a cell-surface receptor; (b) an effector, such as an ion channel or the enzyme adenylate cyclase; and (c) a guanine nucleotide-binding regulatory polypeptide or G protein, that is coupled to both the receptor and its effector.

G protein-coupled receptors mediate the actions of extracellular signals as diverse as light, odorants, peptide hormones and neurotransmitters. Such receptors have been identified in organisms as evolutionarily divergent as yeast and man. Nearly all G protein-coupled receptors bear sequence similarities with one another, and it is thought that all share a similar topological motif consisting of seven hydrophobic (and potentially α-helical) segments that span the lipid bilayer (Dohlman et al., 1987; Dohlman et al., 1991).

G proteins consist of three tightly associated subunits, α, β and γ (1:1:1) in order of decreasing mass. Following agonist binding to the receptor, a conformational change is transmitted to the G protein, which causes the Gα-subunit to exchange a bound GDP for GTP and to dissociate from the βγ-subunits. The GTP-bound form of the α-subunit is typically the effector-modulating moiety. Signal amplification results from the ability of a single receptor to activate many G protein molecules, and from the stimulation by Gα-GTP of many catalytic cycles of the effector.

The family of regulatory G proteins comprises a multiplicity of different α-subunits (greater than twenty in man), which associate with a smaller pool of β- and γ-subunits (greater than four each) (Strothman and Simon, 1991). Thus, it is anticipated that differences in the α-subunits probably distinguish the various G protein oligomers, although the targeting or function of the various α-subunits might also depend on the βγ subunits with which they associate (Strothman and Simon, 1991).

Improvements in cell culture and in pharmacological methods, and more recently, use of molecular cloning and gene expression techniques have led to the identification and characterization of many seven-transmembrane segment receptors, including new sub-types and sub-sub-types of previously identified receptors. The $\alpha_1$ and $\alpha_2$-adrenergic receptors once thought to each consist of single receptor species, are now known to each be encoded by at least three distinct genes (Kobilka et al., 1987; Regan et al., 1988;

Cotecchia et al., 1988; Lomasney, 1990). In addition to rhodopsin in rod cells, which mediates vision in dim light, three highly similar cone pigments mediating color vision have been cloned (Nathans et al., 1986A; and Nathans et al., 1986B). All of the family of G protein-coupled receptors appear to be similar to other members of the family of G protein-coupled receptors (e.g., dopaminergic, muscaric, serotonergic, tachykinin, etc.), and each appears to share the characteristic seven-transmembrane segment topography.

When comparing the seven-transmembrane segment receptors with one another, a discernible pattern of amino acid sequence conservation is observed. Transmembrane domains are often the most similar, whereas the amino and carboxyl terminal regions and the cytoplasmic loop connecting transmembrane segments V and VI can be quite divergent (Dohlman et al., 1987).

Interaction with cytoplasmic polypeptides, such as kinases and G proteins, was predicted to involve the hydrophobic loops connecting the transmembrane domains of the receptor. The challenge, however, has been to determine which features are preserved among the seven-transmembrane segment receptors because of conservation of function, and which divergent features represent structural adaptations to new functions. A number of strategies have been used to test these ideas, including the use of recombinant DNA and gene expression techniques for the construction of substitution and deletion mutants, as well as of hybrid or chimeric receptors (Dohlman et al., 1991).

With the growing number of receptor sub-types, G-protein subunits, and effectors, characterization of ligand binding and G protein recognition properties of these receptors is an important area for investigation. It has long been known that multiple receptors can couple to a single G protein and, as in the case of epinephrine binding to $\beta_2$- and $\alpha_2$-adrenergic receptors, a single ligand can bind to multiple functionally distinct receptor sub-types. Moreover, G proteins with similar receptor and effector coupling specificities have also been identified. For example, three species of human $G_i$ have been cloned (Itoh et al., 1988), and alternate mRNA splicing has been shown to result in multiple variants of $G_s$ (Kozasa et al., 1988). Cloning and over production of the muscarinic and $\alpha_2$-adrenergic receptors led to the demonstration that a single receptor sub-type, when expressed at high levels in the cell, will couple to more than one type of G protein.

Opioid receptors are known to be sensitive to reducing agents, and the occurrence of a disulfide bridge has been postulated as essential for ligand binding (Gioannini et al., 1989). For rhodopsin, muscarinic, and $\beta$-adrenergic receptors, two conserved cysteine residues in each of the two first extracellular loops have been shown critical for stabilizing the functional protein structure and are presumed to do so by forming a disulfide bridge. Structure/function studies of opioid ligands have shown the importance of a protonated amine group for binding to the receptor with high affinity. The binding site of the receptor might, therefore, possess a critical negatively charged counterpart Catecholamine receptors display in their sequence a conserved aspartate residue that has been shown necessary for binding the positively charged amine group of their ligands.

Given the complexity and apparent degeneracy of function of various opioid receptors, a question of fundamental importance is how, and under what circumstances do specific sub-type and sub-sub-type receptors exert their physiological effect in the presence of the appropriate stimulatory ligand. A traditional approach to answering this question has been to reconstitute the purified receptor and G protein components in vitro. Unfortunately, purification schemes have been successful for only a very limited number of receptor sub-types and their cognate G-proteins. Alternatively, heterologous expression systems can be of more general usefulness in the characterization of cloned receptors and in elucidating receptor G protein coupling specificity (Marullo et al., 1988; Payette et al., 1990; King et al., 1990).

One such system was recently developed in yeast cells, in which the genes for a mammalian $\beta_2$-adrenergic receptor and $G_s$ $\alpha$-subunit were coexpressed (King et al., 1990). Expression of the $\beta_2$-adrenergic receptor to levels several hundred-fold higher than in any human tissue was attained, and ligand binding was shown to be of the appropriate affinity, specificity, and stereoselectivity. Moreover, a $\beta_2$-adrenergic receptor-mediated activation of the pheromone signal transduction pathway was demonstrated by several criteria, including imposition of growth arrest, morphological changes, and induction of a pheromone-responsive promoter (FUS1) fused to the *Escherichia coli* lacZ gene (encoding $\beta$-galactosidase) (King et al., 1990).

Finally, expression of a single receptor in the absence of other related sub-types is often impossible to achieve, even in isolated, non-recombinant mammalian cells. Thus, there has been considerable difficulty in applying the standard approaches of classical genetics or even the powerful techniques of molecular biology to the study of opioid receptors. In particular, means are needed for the identification of the DNA sequences encoding individual opioid receptors. Given such isolated, recombinant sequences, it is possible to address the heretofore intractable problems associated with design and testing of isoform-specific opioid receptor agonists and antagonists. The availability of cDNAs encoding the opioid receptors will permit detailed studies of signal-transduction mechanisms and reveal the anatomical distribution of the mRNAs of these receptors, providing information on their expression pattern in the nervous system. This information should ultimately allow better understanding of the opioid system in analgesia, and also the design of more specific therapeutic drugs.

Availability of polynucleotide sequences encoding opioid receptors, and the polypeptide sequences of the encoded receptors, will significantly increase the capability to design pharmaceutical compositions, such as analgesics, with enhanced specificity of function. In general, the availability of these polypeptide sequences will enable efficient screening of candidate compositions. The principle in operation through the screening process is straightforward: natural agonists and antagonists bind to cell-surface receptors and channels to produce physiological effects; certain other molecules bind to receptors and channels; therefore, certain other molecules may produce physiological effects and act as therapeutic pharmaceutical agents. Thus, the ability of candidate drugs to bind to opioid receptors can function as an extremely effective screening criterion for the selection of pharmaceutical compositions with a desired functional efficacy.

Prior methods for screening candidate drug compositions based on their ability to preferentially bind to cell-surface receptors has been limited to tissue-based techniques. In these techniques, animal tissues rich in the receptor type of interest are extracted and prepared; candidate drugs are then allowed to interact with the prepared tissue and those found to bind to the receptors are selected for further study. However, these tissue-based screening techniques suffer from several significant disadvantages. First, they are expensive because the source of receptor cell tissue—laboratory animals—is expensive. Second, extensive technical input is required to operate the screens. And, third, the screens may confuse the results because there are no tissues where only one receptor subtype is expressed exclusively. With traditional prior art screens you are basically looking at the wrong interactions or, at best, the proper interactions mixed in with a whole variety of unwanted interactions. An additional fundamental deficiency of animal tissue screens is that they contain animal receptors—ideal for the development of drugs for animals but of dubious value in human therapeutic agents.

The solution to this problem provided by the present invention is obvious. A polynucleotide of the present invention, transfected into suitable host cells, can express polypeptide sequences corresponding to opioid receptors, both in large quantities and through relatively simple laboratory procedures. The result is the availability of extremely specific receptor-drug interactions free from the competitive and unwanted interactions encountered in tissue-based screens. Further expression in a microorganism where no such endogenous receptors exist (e.g. yeast cells or mutant mammalian cell lines) can be useful for screening and evaluating sub-type-selective drugs (Marullo et a, 1988; Payette et al., 1990; and King et al., 1990).

BRIEF SUMMARY OF THE INVENTION

In one aspect, the present invention provides an isolated and purified polynucleotide that encodes a mu opioid receptor polypeptide and a transcription regulatory polypeptide. In a preferred embodiment, a polynucleotide of the present invention is a DNA molecule. Even more preferred, a polynucleotide of the present invention encodes a polypeptide comprising the amino acid residue sequence of SEQ ID NO:2 or SEQ ID NO:4. Most preferably, an isolated and purified polynucleotide of the invention comprises the nucleotide base sequence of SEQ ID NO:1 or SEQ ID NO:3.

Yet another aspect of the present invention contemplates an isolated and purified polynucleotide comprising a base sequence that is identical or complementary to a segment of at least 10 contiguous bases of SEQ ID NO:1 or SEQ ID NO:3, wherein the polynucleotide hybridizes to a polynucleotide that encodes a mu opioid receptor polypeptide. Preferably, an isolated and purified polynucleotide comprises a base sequence that is identical or complementary to a segment of at least 25 to 70 contiguous bases of SEQ ID NO:1 or SEQ ID NO:3. For example, a polynucleotide of the invention can comprise a segment of bases identical or complementary to 40 to 55 contiguous bases of the disclosed nucleotide sequences.

In still another embodiment of the present invention, there is provided an isolated and purified polynucleotide comprising a base sequence that is identical or complementary to a segment of at least 10 contiguous bases of SEQ ID NO:1. The polynucleotide of the invention hybridizes to SEQ ID NO:1, or a complement of SEQ ID NO:1. Preferably, the isolated and purified polynucleotide comprises a base sequence that is identical or complementary to a segment of at least 25 to 70 contiguous bases of SEQ ID NO:1. For example, the polynucleotide of the invention can comprise a segment of bases identical or complementary to 40 to 55 contiguous bases of SEQ ID NO:1.

Alternatively, the present invention contemplates an isolated and purified polynucleotide that comprises a base sequence that is identical or complementary to a segment of at least 10 contiguous bases of SEQ ID NO:3. The polynucleotide of the invention hybridizes to SEQ ID NO:3, or a complement of SEQ ID NO:3. Preferably, the polynucleotide comprises a base sequence that is identical or complementary to a segment of at least 25 to 70 contiguous bases of SEQ ID NO:3. For example, the polynucleotide can comprise a segment of bases identical or complementary to 40 to 55 contiguous bases of SEQ ID NO:3.

In another embodiment, the present invention contemplates an isolated and purified mu opioid receptor polypeptide or a gene transcription regulatory polypeptide. Preferably, a polypeptide of the invention is a recombinant polypeptide. Even more preferably, an opioid receptor polypeptide of the present invention comprises the amino acid residue sequence of SEQ ID NO:2 and a gene transcription regulatory polypeptide of the present invention comprises the amino acid residue sequence of SEQ ID NO:4.

In an alternative embodiment, the present invention provides an expression vector comprising a polynucleotide that encodes a mu opioid receptor polypeptide. Preferably, an expression vector of the present invention comprises a polynucleotide that encodes a polypeptide comprising the amino acid residue sequence of SEQ ID NO:2 or SEQ ID NO:4. More preferably, an expression vector of the present invention comprises a polynucleotide comprising the nucleotide base sequence of SEQ ID NO:1 or SEQ ID NO:3. Even more preferably, an expression vector of the invention comprises a polynucleotide operatively linked to an enhancer-promoter. More preferably still, an expression vector of the invention comprises a polynucleotide operatively linked to a prokaryotic promoter. Alternatively, an expression vector of the present invention comprises a polynucleotide operatively linked to an enhancer-promoter that is a eukaryotic promoter, and the expression vector further comprises a polyadenylation signal that is positioned 3' of the carboxyl-terminal amino acid and within a transcriptional unit of the encoded polypeptide.

In yet another embodiment, the present invention provides a recombinant host cell transfected with a polynucleotide that encodes a mu opioid receptor polypeptide. Preferably, a recombinant host cell of the present invention is transfected with the polynucleotide of SEQ ID NO:1 or SEQ ID NO:3. Even more preferably, a host cell of the invention is a eukaryotic host cell. Still more preferably, a recombinant host cell of the present invention is a yeast cell. Alternatively, a recombinant host cell of the invention is a COS or CHO cell. In another aspect, a recombinant host cell of the present invention is a prokaryotic host cell. Preferably, a recombinant host cell of the invention is a bacterial cell of the DH5α strain of *Escherichia coli*. More preferably, a recombinant host cell comprises a polynucleotide under the transcriptional control of regulatory signals functional in the recombinant host cell, wherein the regulatory signals appropriately control expression of a mu opioid receptor polypeptide in a manner to enable all necessary transcriptional and post-transcriptional modification.

In yet another embodiment, the present invention contemplates a process of preparing a mu opioid receptor polypeptide comprising transfecting a cell with polynucleotide that encodes a mu opioid receptor polypeptide to produce a transformed host cell and maintaining the transformed host cell under biological conditions sufficient for expression of the polypeptide. Preferably, the transformed host cell is a eukazyotic cell. More preferably still, the eukaryotic cell is a COS or CHO cell. Alternatively, the host cell is a prokaryotic cell. More preferably, the prokaryotic cell is a bacterial cell of the DH5α strain of *Escherichia coli*.

Even more preferably, a polynucleotide transfected into the transformed cell comprises the nucleotide base sequence of SEQ ID NO:1 or SEQ ID NO:3.

In still another embodiment, the present invention provides an antibody immunoreactive with a mu opioid receptor polypeptide. Preferably, an antibody of the invention is a monoclonal antibody. More preferably, a mu opioid receptor polypeptide comprises the amino acid residue sequence of SEQ ID NO:2 or SEQ ID NO:4.

In another aspect, the present invention contemplates a process of producing an antibody immunoreactive with a mu opioid receptor polypeptide comprising the steps of (a) transfecting a recombinant host cell with a polynucleotide that encodes a mu opioid receptor polypeptide; (b) culturing the host cell under conditions sufficient for expression of the polypeptide; (c) recovering the polypeptide; and (d) preparing the antibody to the polypeptide. Preferably, the host cell is transfected with the polynucleotide of SEQ ID NO:1 or SEQ ID NO:3. Alternatively, steps (a), (b) and (c) can be avoided by use of a synthetic polypeptide. Even more preferably, the present invention provides an antibody prepared according to the process described above.

Alternatively, the present invention provides a process of detecting a mu opioid receptor polypeptide, wherein the process comprises immunoreacting the polypeptide with an antibody prepared according to the process described above to form an antibody-polypeptide conjugate, and detecting the conjugate.

In yet another embodiment, the present invention contemplates a process of detecting a messenger RNA transcript that encodes a mu opioid receptor polypeptide, wherein the process comprises (a) hybridizing the messenger RNA transcript with a polynucleotide sequence that encodes the mu opioid receptor polypeptide to form a duplex; and (b) detecting the duplex. Alternatively, the present invention provides a process of detecting a DNA molecule that encodes a mu opioid receptor polypeptide, wherein the process comprises (a) hybridizing DNA molecules with a polynucleotide that encodes a mu opioid receptor polypeptide to form a duplex; and (b) detecting the duplex.

In another aspect, the present invention contemplates a diagnostic assay kit for detecting the presence of a mu opioid receptor polypeptide in a biological sample, where the kit comprises a first container containing a first antibody capable of immunoreacting with a mu opioid receptor polypeptide, with the first antibody present in an amount sufficient to perform at least one assay. Preferably, an assay kit of the invention further comprises a second container containing a second antibody that immunoreacts with the first antibody. More preferably, the antibodies used in an assay kit of the present invention are monoclonal antibodies. Even more preferably, the first antibody is affixed to a solid support. More preferably still the first and second antibodies comprise an indicator, and, preferably, the indicator is a radioactive label or an enzyme.

In an alternative aspect, the present invention provides a diagnostic assay kit for detecting the presence, in biological samples, of a polynucleotide that encodes a mu opioid receptor polypeptide, the kit comprising a first container that contains a second polynucleotide identical or complementary to a segment of at least 10 contiguous nucleotide bases of SEQ ID NO:1 or SEQ ID NO:3.

In another embodiment, the present invention contemplates a diagnostic assay kit for detecting the presence, in a biological sample, of an antibody immunoreactive with a mu opioid receptor polypeptide, the kit comprising a first container containing a mu opioid receptor polypeptide that immunoreacts with the antibody, with the polypeptide present in an amount sufficient to perform at least one assay.

In yet another aspect, the present invention contemplates a process of screening substances for their ability to interact with a mu opioid receptor polypeptide comprising the steps of providing a mu opioid receptor polypeptide, and testing the ability of selected substances to interact with the opioid receptor polypeptide.

In a preferred embodiment, providing a mu opioid receptor polypeptide is transfecting a host cell with a polynucleotide that encodes a mu opioid receptor polypeptide to form a transformed cell and maintaining the transformed cell under biological conditions sufficient for expression of the opioid receptor polypeptide.

BRIEF DESCRIPTION OF THE DRAWINGS

In the drawings which form a portion of the specification it is shown that in FIG. 1A and FIG. 1B amino acid sequence alignment of MOR-1, the mu opioid receptor, with the mouse δ-opioid receptor (DOR-1) (Evans et al., 1992) and the rat somatostatin receptor (SOM1 and SOM2) (Meyerhof et al., 1991; Kluxen et al., 1992). Seven hydrophobic domains are underlined and numbered I to VII.-, Amino acids identical to those in MOR-1. Spaces, gaps introduced for alignment, diamond figure, putative N-linked glycosylation sites; downward arrow, potential site for phosphorylation by CAMP-dependent protein kinase; O, potential sites for phosphorylation by protein kinase C; , conserved aspartic acid residues proposed to interact with the amine group of ligands; =, conserved cysteine residues that might form a disulfide bond; ♦, potential pahnitoylation site. The sequence for the MOR-1 cDNA has been submitted to GenBank (accession number L13069).

It is shown in FIG. 2 that saturation binding of [$^3$H] diprenorphine using COS-7 cell membranes. [$^3$H] Diprenorphine binding was determined using membranes prepared from COS-7 cells transfected with either the rat MOR-1 cDNA plasmid (●) or the parental vector (○). Data from a representative experiment are presented and are expressed as mean ± standard error. Inset, Scatchard plot analysis of the binding data from MOR-1-transfected cells.

Figure 3A:
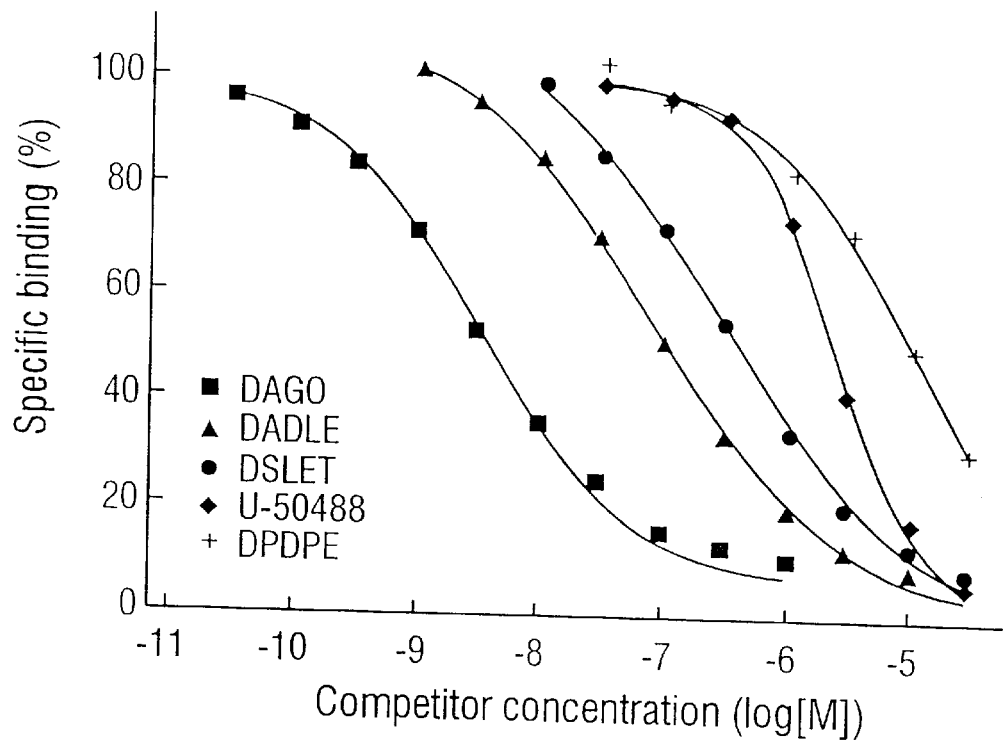
Figure 3B:
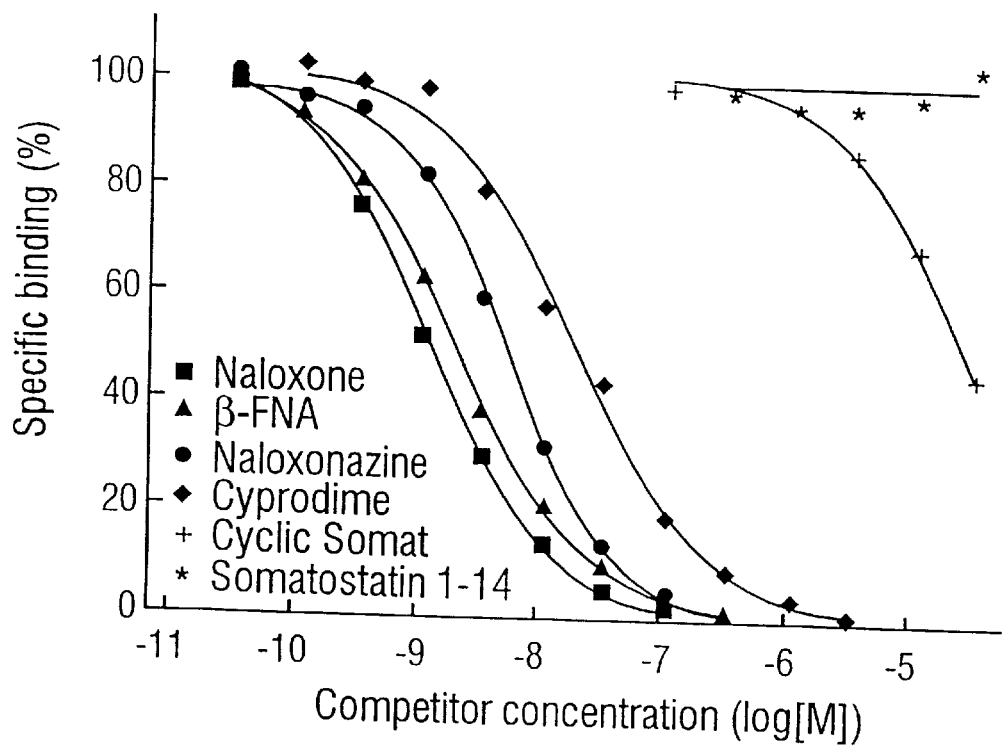

It is shown in FIG. 3A and FIG. 3B that displacement of [$^3$H]diprenorphine binding with unlabeled ligands as competitors. Data from a representative experiment are presented for each ligand. Top, using opioid agonists as competitors; bottom, using opioid antagonists and somatostatins as competitors.

Figure 4:
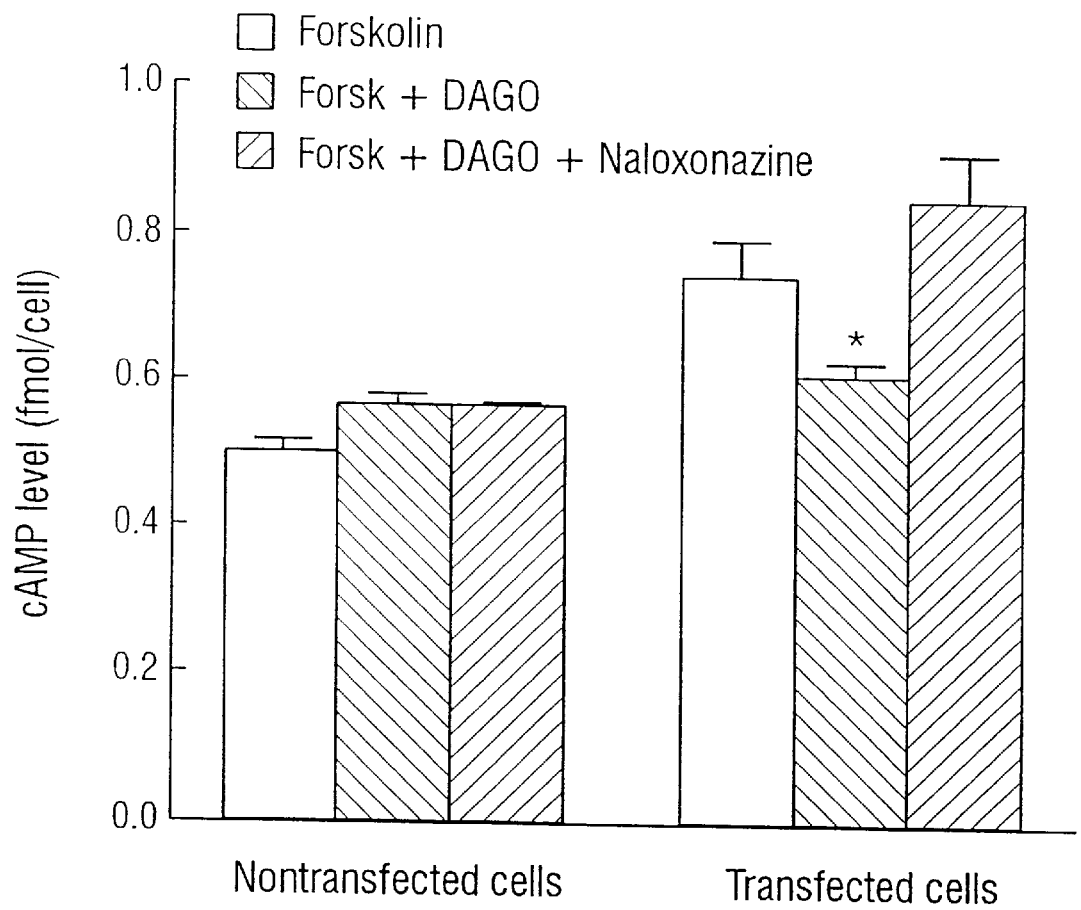

It is shown in FIG. 4 that functional coupling of MOR-1 to adenylyl cyclase. Parental COS-7 cells (Nontransfected cells) or COS-7 cells expressing MOR-1 (Transfected cells) were stimulated with forskolin (Forsk.) to elevate adenylyl cyclase activity above basal levels. The μ-selective ligands were included during forskolin treatment as indicated. Cellular cAMP levels were determined. Data are expressed as mean ± standard error (four experiments). *, Data are significantly different from the control group (transfected cells treated with forskolin only).

DETAILED DESCRIPTION OF THE INVENTION

I. The Invention

The present invention provides DNA segments, purified polypeptides, methods for obtaining antibodies, methods of cloning and using recombinant host cells necessary to obtain and use recombinant mu opioid receptors. Thus, the difficulties encountered with applying the standard approaches of classical genetics or techniques in molecular biology evident in the prior art to mu opioid receptors, have been overcome. Accordingly, the present invention concerns generally compositions and methods for the preparation and use of mu opioid receptors.

II. Polynucleotide

A. Isolated and Purified Polynucleotides That Encode mu Opioid Receptor Polypeptides In one aspect, the present invention provides an isolated and purified polynucleotide that encodes a mu opioid receptor polypeptide. In a preferred embodiment, the polynucleotide of the present invention is a DNA molecule. Even more preferred, a polynucleotide of the present invention encodes a polypeptide comprising the amino acid residue sequence of SEQ ID NO:2 or SEQ ID NO:4. Most preferably, an isolated and purified polynucleotide of the invention comprises the nucleotide base sequence of SEQ ID NO:1 or SEQ ID NO:3.

As used herein, the term "polynucleotide" means a sequence of nucleotides connected by phosphodiester linkages. Polynucleotides are presented herein in the direction from the 5' to the 3' direction. A polynucleotide of the present invention can comprise from about 680 to about several hundred thousand base pairs. Preferably, a polynucleotide comprises from about 680 to about 150,000 base pairs. Preferred lengths of particular polynucleotide are set forth hereinafter.

A polynucleotide of the present invention can be a deoxyribonucleic acid (DNA) molecule or ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), inosine (I) and uracil (U).

A polynucleotide of the present invention can be prepared using standard techniques well known to one of skill in the art. The preparation of a cDNA molecule encoding a mu opioid receptor polypeptide of the present invention is described hereinafter in Examples 1 and 2. A polynucleotide can also be prepared from genomic DNA libraries using lambda phage technologies.

In another aspect, the present invention provides an isolated and purified polynucleotide that encodes a mu opioid receptor polypeptide, where the polynucleotide is preparable by a process comprising the steps of constructing a library of cDNA clones from a cell that expresses the polypeptide; screening the library with a labelled cDNA probe prepared from RNA that encodes the polypeptide; and selecting a clone that hybridizes to the probe. Preferably, the polynucleotide of the invention is prepared by the above process. More preferably, the polynucleotide of the invention encodes a polypeptide that has the amino acid residue sequence of SEQ ID NO:2 or SEQ ID NO:4. More preferably still, the polynucleotide comprises the nucleotide sequence of SEQ ID NO:1 or SEQ ID NO:3.

B. Probes and Primers

In another aspect, DNA sequence information provided by the present invention allows for the preparation of relatively short DNA (or RNA) sequences having the ability to specifically hybridize to gene sequences of the selected polynucleotide disclosed herein. In these aspects, nucleic acid probes of an appropriate length are prepared based on a consideration of a selected nucleotide sequence, e.g., a sequence such as that shown in SEQ ID NO:1. The ability of such nucleic acid probes to specifically hybridize to a polynucleotide encoding a mu opioid receptor lends them particular utility in a variety of embodiments. Most importantly, the probes can be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a gene or polynucleotide that encodes a mu opioid receptor polypeptide from mammalian cells using PCR™ technology.

To provide certain of the advantages in accordance with the present invention, a preferred nucleic acid sequence employed for hybridization studies or assays includes probe molecules that are complementary to at least a 10 to 70 or so long nucleotide stretch of a polynucleotide that encodes a mu opioid receptor polypeptide, such as that shown in SEQ ID NOS:1 or 3. A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 25 to 40 nucleotides, 55 to 70 nucleotides, or even longer where desired. Such fragments can be readily prepared by, for example, directly synthesizing the fragment by chemical means, by application of nucleic acid reproduction technology, such as the PCR™ technology of U.S. Pat. No. 4,683,202, herein incorporated by reference, or by excising selected DNA fragments from recombinant plasmids containing appropriate inserts and suitable restriction enzyme sites.

In another aspect, the present invention contemplates an isolated and purified polynucleotide comprising a base sequence that is identical or complementary to a segment of at least 10 contiguous bases of SEQ ID NO:1 or SEQ ID NO:3, wherein the polynucleotide hybridizes to a polynucleotide that encodes a mu opioid receptor polypeptide. Preferably, the isolated and purified polynucleotide comprises a base sequence that is identical or complementary to a segment of at least 25 to 70 contiguous bases of SEQ ID NO:1 or SEQ ID NO:3. For example, the polynucleotide of the invention can comprise a segment of bases identical or complementary to 40 or 55 contiguous bases of the disclosed nucleotide sequences.

Accordingly, a polynucleotide probe molecule of the invention can be used for its ability to selectively form duplex molecules with complementary stretches of the gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids. For example, one will select relatively low salt and/or high temperature conditions, such as provided by 0.02M–0.15M NaCl at temperatures of 50° C. to 70° C. Those conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate a mu opioid receptor polypeptide coding sequence from other cells, functional equivalents, or the like, less stringent hybridization conditions are typically needed to allow formation of the heteroduplex. In these circumstances, one can desire to employ conditions such as 0.15M–0.9M salt, at temperatures ranging from 20° C. to 70° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In still another embodiment of the present invention, there is provided an isolated and purified polynucleotide comprising a base sequence that is identical or complementary to a segment of at least 10 contiguous bases of SEQ ID NO:1. The polynucleotide of the invention hybridizes to SEQ ID NO:1, or a complement of SEQ ID NO:1. Preferably, the isolated and purified polynucleotide comprises a base sequence that is identical or complementary to a segment of at least 25 to 70 contiguous bases of SEQ ID NO:1. For example, the polynucleotide of the invention can comprise a segment of bases identical or complementary to 40 to 55 contiguous bases of SEQ ID NO:1.

Alternatively, the present invention contemplates an isolated and purified polynucleotide that comprises a base sequence that is identical or complementary to a segment of at least 10 contiguous bases of SEQ ID NO:3. The polynucleotide of the invention hybridizes to SEQ ID NO:3, or a complement of SEQ ID NO:3. Preferably, the polynucleotide comprises a base sequence that is identical or complementary to a segment of at least 25 to 70 contiguous bases of SEQ ID NO:3. For example, the polynucleotide can comprise a segment of bases identical or complementary to 40 to 55 contiguous bases of SEQ ID NO:3.

In certain embodiments, it is advantageous to employ a polynucleotide of the present invention in combination with an appropriate label for detecting hybrid formation A wide variety of appropriate labels are known in the art, including radioactive, enzymatic or other ligands, such as avidin/biotin, which are capable of giving a detectable signal.

In general, it is envisioned that a hybridization probe described herein is useful both as a reagent in solution hybridization as well as in embodiments employing a solid phase. In embodiments involving a solid phase, the test DNA (or RNA) is adsorbed or otherwise affixed to a selected matrix or surface. This fixed nucleic acid is then subjected to specific hybridization with selected probes under desired conditions. The selected conditions depend as is well known in the art on the particular circumstances and criteria required (e.g., on the G+C content, type of target nucleic acid, source of nucleic acid, size of hybridization probe). Following washing of the matrix to remove non-specifically bound probe molecules, specific hybridization is detected, or even quantified, by means of the label.

II. Mu Opioid Receptor Polypeptide and Gene Transcription Regulatory Polypeptide In one embodiment, the present invention contemplates an isolated and purified mu opioid receptor polypeptide. Preferably, a mu opioid receptor polypeptide of the invention is a recombinant polypeptide. Even more preferably, a mu opioid receptor polypeptides of the present invention comprises the amino acid residue sequence of SEQ ID NO:2. A mu opioid receptor polypeptide preferably comprises less than about 500 amino acid residues and, more preferably less than about 400 amino acid residues.

In another embodiment, the present invention contemplates an isolated and purified gene transcription regulatory polypeptide. Preferably, a gene transcription regulatory polypeptide of the invention is a recombinant polypeptide. Even more preferably, gene transcription regulatory polypeptides of the present invention comprises the amino acid residue sequence of SEQ ID NO:4. A gene transcription regulatory polypeptide preferably comprises less than about 500 amino acid residues and, more preferably less than about 400 amino acid residues.

Polypeptides are disclosed herein as amino acid residue sequences. Those sequences are written left to right in the direction from the amino to the carboxyl terminus. In accordance with standard nomenclature, amino acid residue sequences are denominated by either a single letter or a three letter code as indicated below.

| Amino Acid Residue | 3-Letter Code | 1-Letter Code |
| --- | --- | --- |
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Modifications and changes can be made in the structure of a polypeptide of the present invention and still obtain a molecule having like opioid receptor characteristics. For example, certain amino acids can be substituted for other amino acids in a sequence without appreciable loss of receptor activity. Because it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like properties.

In making such changes, the hydropathic index of amino acids can be considered. The importance of the hydropathic amino acid index in conferring interactive biologic function on a polypeptide is generally understood in the art (Kyte, J. and R. F. Doolittle 1982). It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. U.S. Pat. No. 4,554,101, incorporated herein by reference, states that the greatest local average hydrophilicity of a polypeptide, as governed by the hydrophilicity of its adjacent amino acids, correlates with its immunogenicity and antigenicity, i.e. with a biological property of the polypeptide.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine (See Table 1, below). The present invention thus contemplates functional or biological equivalents of a mu opioid receptor polypeptide as set forth above.

TABLE 1

| Original Residue | Exemplary Substitutions |
| --- | --- |
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Met; Leu; Tyr |
| Ser | Thr |
| Thr | Ser |
| Trp | Tyr |

TABLE 1-continued

| Original Residue | Exemplary Substitutions |
| --- | --- |
| Tyr | Trp; Phe |
| Val | Ile; Leu |

Biological or functional equivalents of a polypeptide can also be prepared using site-specific mutagenesis. Site-specific mutagenesis is a technique useful in the preparation of second generation polypeptides, or biologically functional equivalent polypeptides or peptides, derived from the sequences thereof, through specific mutagenesis of the underlying DNA. As noted above, such changes can be desirable where amino acid substitutions are desirable. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by Adelman et al., (1983). As will be appreciated, the technique typically employs a phage vector which can exist in both a single stranded and double stranded form. Typical vectors useful in site-directed mutagenesis include vectors such as the M13 phage (Messing et al., 1981). These phage are commercially available and their use is generally known to those of skill in the art.

In general, site-directed mutagenesis in accordance herewith is performed by first obtaining a single-stranded vector which includes within its sequence a DNA sequence which encodes all or a portion of the mu opioid receptor polypeptide sequence selected. An oligonucleotide primer bearing the desired mutated sequence is prepared, generally synthetically, for example, by the method of Crea et al., (1978). This primer is then annealed to the singled-stranded vector, and extended by the use of enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as E. coli cells and clones are selected which include recombinant vectors bearing the mutation. Commercially available kits come with all the reagents necessary, except the oligonucleotide primers.

Amino acid residues can be added to or deleted from the mu opioid receptor polypeptide through the use of standard molecular biological techniques without altering the functionality of the receptor. For example, portions of the mu opioid receptor can be removed to create truncated opioid receptors. The truncated receptor retains the properties of mu opioid receptors such as ligand binding and the ability to interact with other proteins (G proteins, adenylyl cyclase, for example). Functional truncated proteins have been reported for phosphodiesterases, ion channels, and membrane transporters. As used herein, truncated receptors are receptors in which amino acids have been removed from the wild type receptor to create a shorter receptor or portions thereof. As used herein, chimeric receptors are receptors in which amino acids have been added to the receptor. A chimeric receptor can be shorter, longer or the same length as the wild type receptor.

The functional activity of truncated and chimeric receptors have been demonstrated in a number of receptor systems. In particular, truncated and chimeric adrenergic receptors, which are structurally similar to the opioid receptors, have been shown to retain functional properties of the wild type adrenergic receptor.

Most of the long carboxyl terminus of the avian β-adrenergic receptor can be deleted or proteolytically removed without altering the ligand-binding properties or regulatory properties of the receptor. The ligand binding properties of five truncated β-adrenergic receptors for both agonists and antagonists were found to be similar to those of the wild type receptor. Furthermore, truncated adrenergic receptors also stimulated adenylyl cyclase activity. In fact, truncated β-adrenergic receptors, in the presence of agonists, showed a greater stimulation of adenylyl cyclase activity than the stimulation achieved by the wild type receptor. (Parker et al., 1991).

Similar results were obtained for the α-adrenergic receptor. A truncated α-adrenergic receptor activated phosphatidyl inositol hydrolysis as effectively as wild type a-adrenergic receptor. (Cotecchia et al., 1989).

Functional chimeric receptors have also been created by a number of investigators. Functional chimeric adrenergic receptors were created by splicing together sections of the $\alpha_2$ and $\beta_2$ adrenergic receptors. (Kobilka et al., 1988). Functional chimeras have also been generated for the following receptors: between $\beta_1$ and $\beta_2$ receptors, (Fnelle et al., 1988; Marullo et al., 1990); between m2 and m3 muscarinic receptors, (Wess et al. 1990); between m1 muscarinic and β adrenergic receptors, (Wong et al., (1990); between $D_2$ dopamine and m1 muscarinic receptors, (England et al., 1991); between luteinizing hormone and β adrenergic receptors, (Moyle et al., 1991); between $NK_1$ and $NK_3$ substance P receptors, (Gether et al., 1993); and platelet-derived growth factor and epidermal growth factor receptors, (Seedorf et al., 1991).

Chimeric mu opioid receptors can be created by splicing sections of a second receptor to a mu receptor. The two receptors can be similar to each other. Thus, for the creation of chimeric mu opioid receptors, other opioid receptors, such as sigma, delta, and kappa opioid receptors, are ideal sources for nucleotide sequences. For example, a transmembrane domain in the mu opioid receptor can be substituted with an analogous transmembrane domain from sigma, delta or kappa opioid receptor. It is contemplated that the nucleotide source of the second receptor is not limited to opioid receptors. Chimeric receptors can be created from mu opioid receptor and other similar receptors such as acetylcholine, adenosine, adrenergic, angiotensin, bombesin, bradykinin, cannabinoid, dopamine, endothelin, histamine, interleukin, luteinizing hormone, neuromedin K, neuropeptide Y, odorant, prostaglandin, parathyroid hormone, serotonin, somatostatin, substance K, substance P, thrombin, thromboxane A2, thyrotropin releasing hormone and vasopressin receptors.

A mu opioid receptor polypeptide of the present invention is understood not to be limited to a particular source. As disclosed herein, the techniques and compositions of the present invention provide, for example, the identification and isolation of mu opioid receptors from rodent sources. Thus, the invention provides for the general detection and isolation of the genus of mu opioid receptor polypeptides from a variety of sources. It is believed that a number of species of the family of mu opioid receptor polypeptides are amenable to detection and isolation using the compositions and methods of the present inventions.

A polypeptide of the present invention is prepared by standard techniques well known to those skilled in the art. Such techniques include, but are not limited to, isolation and purification from tissues known to contain that polypeptide, and expression from cloned DNA that encodes such a polypeptide using transformed cells (See Examples 1 and 2, hereinafter).

Opioid receptor polypeptides are found in virtually all mammals including human. The sequence of a mouse delta opioid receptor has been previously described (Kieffer et al., 1992; Evans et al., 1992). As is the case with other receptors, there is likely little variation between the structure and function of an opioid receptor in different species. Where there is a difference between species, identification of those differences is well within the skill of an artisan. Thus, the present invention contemplates a mu opioid receptor polypeptide from any mammal. A preferred mammal is a rodent or a human.

Regulation of gene expression in a cell is accomplished through many different mechanisms. A well known mechanism of gene expression regulation is through the use of a zinc finger motif in a transcription regulatory polypeptide. The zinc finger domain found in many transcription factors binds to DNA to regulate transcription. Zinc finger domains are nucleic acid-binding protein structures first identified in the Xenopus transcription factor TFIIIA. These domains have since been found in numerous nucleic acid-binding proteins. (Klug A. and D. Rhodes, 1987; Evans, R. M. and S. M. Hollenberg, 1988; Payre, F., and A. Vincent, 1988; Miller, J. et al., 1985; Berg J. M., 1988).

A zinc finger domain is composed of 25 to 30 amino acid residues. There are two cysteine or histidine residues at both extremities of the domain, which are most probably involved in the tetrahedral coordination of a zinc atom Each zinc finger likely binds to the major groove of B-DNA so as to interact with ~5 successive base pairs; that is, with about a half-turn of B-DNA. A zinc finger protein thus can bind to DNA in which the protein binds along one face of the DNA with successive zinc fingers bound in the major groove on alternate sides of the double helix. Zinc fingers likely form structural "scaffolds" that match the double helix's three dimensional contour. Base sequence specificity is presumably provided by the particular sequence of each zinc finger's variable residues. (Klug, A and D. Rhodes, 1987). A schematic representation of a zinc finger domain is shown on the next page:

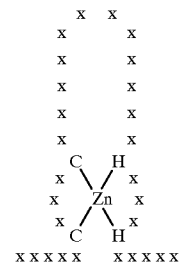

Zinc fingers have been identified in many transcription factors including Sp1, estrogen, and glucocorticoid receptors, several Drosophila developmental regulators, and the Xenopus Xfin protein, as well as in the *E. coli* UvrA protein and certain retroviral nucleic acid binding proteins.

Xenopus transcription factor IIIA (TFIIIA) is a regulatory protein which contains nine zinc fingers. The 344-residue TFIIIA contains 9 similar, tandemly repeated, ~30-residue units, each of which contains two invariant cysteine residues, two invariant histidine residues, and several conserved hydrophobic residues. Each of these units binds a $Zn^{2+}$ ion. X-ray absorption measurements indicate that the $Zn^{2+}$ ion is tetrahedrally coordinated to the invariant cysteine and histidine residues. Sequence analysis of a number of transcription regulators has revealed that the zinc finger motif occurs between about 2 to 40 times in a transcription regulator.

Two major classes of zinc fingers are characterized according to the number and positions of the histidine and cysteine residues involved in the zinc atom coordination. In the first class, called C2H2, the first pair of zinc coordinating residues are cysteines, while the second pair are histidines. Transcription factor TFIIIA is the prototype example for this class of zinc fingers. A number of experimental reports have demonstrated the zinc-dependent DNA or RNA binding property of some members of this class. The other class of zinc fingers, called C4, groups together many different regulatory proteins that happen to have several cysteines within a short stretch of sequence. The steroid hormone receptors are an example of proteins belonging to this class.

Some of the proteins which are known to include C2H2-type zinc fingers are listed below. We have indicated, between brackets, the number of zinc finger regions found in each of these proteins; a '+' symbol indicates that only partial sequence data is available and that additional finger domains may be present.

Xenopus: transcription factor TFIIIA (9), Xfin (37), XlcOF10 (7), XlcOF22 (12).

Drosophila: Glass (5), Hunchback (6), Kruppel (5), Kruppel-H (4+), Snail(5), Serependity locus beta (6), delta (7), and h-1 (8), Suppressor of hairy wing su(Hw) (12), Tramtrack (2).

Yeast: transcriptional activator ADR1 (2), transcriptional factor SWI5 (3).

*Aspergillus nidulans*: developmental protein br1A (2).

Mammalian: transcription factor Sp1 (3), ZfX (13), ZfY (13), Zfp-35 (18), EGR1/Krox24 (3), EGR2/Krox20 (3), Evi-1 (10), GLI1 (5), GLI2 (4+),GLI3 (3+), KR1 (9+), KR2 (9), KR3 (15+), KR4 (14+), KR5 (11+), HF.10 (10), HF.12 (6+).

Sequence analysis of rat mu opioid receptor reveals that in an alternate reading frame, the cDNA of the mu opioid receptor (SEQ. ID NO:1) codes for a polypeptide which contains a zinc finger motif (SEQ. ID NO:3 and SEQ. ID NO:4). The zinc finger containing polypeptide comprises 298 amino acids encoded by nucleotides 339 to 1235. The zinc finger containing polypeptide is smaller by 100 amino acids than the mu opioid receptor. SEQ. ID NO:3 shows the alternate reading frame of a mu opioid receptor that encodes the transcription regulatory polypeptide. In particular, there is a zinc finger motif, of the C2H2 cass, located between amino acid residues 155 and 178 of this protein. This motif fits the consensus pattern of C-x(2,4)-C-x(12)-H-x(3,5)-H for the C2H2 class, with 4 amino acid residues each in between the two cysteines at the amino end of the motif and the two histidines at the carboxyl end of the motif. The C2H2 zinc finger motif has been found in many proteins, including mammalian transcription factor Sp1 as discussed above.

It is likely that the zinc finger polypeptide of the mu opioid receptor is involved in the autoregulation of the expression of the mu opioid receptor. The polynucleotide that encodes the zinc finger polypeptide and the gene transcription regulatory polypeptide is useful in controlling the expression of the mu opioid receptor. An antibody immunoreactive with the gene transcription regulatory polypeptide can be used to regulate the expression of the mu opioid receptor. Alternatively, anti-sense mRNA can be used to regulate the expression of the mu opioid receptor.

In another embodiment, the polynucleotide that encodes the gene transcription regulatory polypeptide can be used to identify other polynucleotides that encode a mu opioid receptor or a transcription regulatory polypeptide.

III. Expression Vectors

In an alternate embodiment, the present invention provides expression vectors comprising polynucleotide that encode mu opioid receptor polypeptides, or a polynucleotide that encodes a gene transcription regulatory polypeptide. Preferably, expression vectors of the present invention comprise polynucleotides that encode polypeptides comprising the amino acid residue sequence of SEQ ID NO:2 or SEQ ID NO:4. More preferably, expression vectors of the present invention comprise polynucleotides comprising the nucleotide base sequence of SEQ ID NO:1 or SEQ ID NO:3. Even more preferably, expression vectors of the invention comprise polynucleotides operatively linked to an enhancer-promoter. More preferably still, expression vectors of the invention comprise a polynucleotide operatively linked to a prokaryotic promoter. Alternatively, expression vectors of the present invention comprise a polynucleotide operatively linked to an enhancer-promoter that is a eukaryotic promoter. Expression vectors further comprise a polyadenylation signal that is positioned 3' of the carboxyl-terminal amino acid and within a transcriptional unit of the encoded polypeptide.

A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promote" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the present invention can be any enhancer-promoter that drives expression in a cell to be transfected. By employing an enhancer-promoter with well-known properties, the level and pattern of gene product expression can be optimized.

A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (RNA). Transcription-terminating regions are well known in the art. A preferred transcription-terminating region is derived from a bovine growth hormone gene.

An expression vector comprises a polynucleotide that encodes a mu opioid receptor polypeptide. Such a polypeptide is meant to include a sequence of nucleotide bases encoding a mu opioid receptor polypeptide sufficient in length to distinguish said segment from a polynucleotide segment encoding a non-opioid receptor polypeptide. A polypeptide of the invention can also encode biologically functional polypeptides or peptides which have variant amino acid sequences, such as with changes selected based on considerations such as the relative hydropathic score of the amino acids being exchanged. These variant sequences are those isolated from natural sources or induced in the sequences disclosed herein using a mutagenic procedure such as site-directed mutagenesis.

Preferably, expression vectors of the present invention comprise polynucleotides that encode polypeptides comprising the amino acid residue sequence of SEQ ID NO:2 or SEQ ID NO:4. An expression vector can include a mu opioid receptor polypeptide coding region itself of any of the mu opioid receptor polypeptides noted above or it can contain coding regions bearing selected alterations or modifications in the basic coding region of such a mu opioid receptor polypeptide. Alternatively, such vectors or fragments can code larger polypeptides or polypeptides which nevertheless include the basic coding region. In any event, it should be appreciated that due to codon redundancy as well as biological functional equivalence, this aspect of the invention is not limited to the particular DNA molecules corresponding to the polypeptide sequences noted above.

Exemplary vectors include the mammalian expression vectors of the pCMV family including pCMV6b and pCMV6c (Chiron Corp., Emeryville Calif.) and pRc/CMV (Invitrogen, San Diego, Calif.). In certain cases, and specifically in the case of these individual mammalian expression vectors, the resulting constructs can require co-transfection with a vector containing a selectable marker such as pSV2neo. Via co-transfection into a dihydrofolate reductase-deficient Chinese hamster ovary cell line, such as DG44, clones expressing opioid polypeptides by virtue of DNA incorporated into such expression vectors can be detected.

A DNA molecule of the present invention can be incorporated into a vector using a number of techniques which are well known in the art. For instance, the vector pUC18 has been demonstrated to be of particular value. Likewise, the related vectors M13mp18 and M13mp19 can be used in certain embodiments of the invention, in particular, in performing dideoxy sequencing.

An expression vector of the present invention is useful both as a means for preparing quantities of the mu opioid receptor polypeptide-encoding DNA itself, and as a means for preparing the encoded polypeptides. It is contemplated that where mu opioid receptor polypeptides of the invention are made by recombinant means, one can employ either prokaxyotic or eukaryotic expression vectors as shuttle systems. However, in that prokaryotic systems are usually incapable of correctly processing precursor polypeptides and, in particular, such systems are incapable of correctly processing membrane associated eukaryotic polypeptides, and since eukazyotic mu opioid receptor polypeptides are anticipated using the teaching of the disclosed invention, one likely expresses such sequences in eukaryotic hosts. However, even where the DNA segment encodes a eukaryotic mu opioid receptor polypeptide, it is contemplated that prokaryotic expression can have some additional applicability. Therefore, the invention can be used in combination with vectors which can shuttle between the eukaryotic and prokaryotic cells. Such a system is described herein which allows the use of bacterial host cells as well as eukaryotic host cells.

Where expression of recombinant polypeptide of the present invention is desired and a eukaryotic host is contemplated, it is most desirable to employ a vector, such as a plasmid, that incorporates a eukaryotic origin of replication. Additionally, for the purposes of expression in eukaryotic systems, one desires to position the opioid receptor encoding sequence adjacent to and under the control of an effective eukaryotic promoter such as promoters used in combination with Chinese hamster ovary cells. To bring a coding sequence under control of a promoter, whether it is eukaryotic or prokaryotic, what is generally needed is to position the 5' end of the translation initiation side of the proper translational reading frame of the polypeptide between about 1 and about 50 nucleotides 3' of or downstream with respect to the promoter chosen. Furthermore, where eukaryotic expression is anticipated, one would typically desire to incorporate into the transcriptional unit which includes the mu opioid receptor polypeptide, an appropriate polyadenylation site.

The pRc/CMV vector (available from Invitrogen) is an exemplary vector for expressing a mu opioid receptor or a gene transcription regulatory polypeptide in mammalian cells, particularly COS and CHO cells. A polypeptide of the present invention under the control of a CMV promoter can be efficiently expressed in mammalian cells. A detailed description of using and expressing a mu opioid receptor in the vector pRc/CMV is provided in examples 2 and 3 of the present application.

pCMV vectors is another exemplary vector. The pCMV plasmids are a series of mammalian expression vectors of particular utility in the present invention. The vectors are designed for use in essentially all cultured cells and work extremely well in SV40-transformed simian COS cell lines. The pCMV1, 2, 3, and 5 vectors differ from each other in certain unique restriction sites in the polylinker region of each plasmid. The pCMV4 vector differs from these 4 plasmids in containing a translation enhancer in the sequence prior to the polylinker. While they are not directly derived from the pCMV1–5 series of vectors, the functionally similar pCMV6b and c vectors are available from the Chiron Corp. of Emeryville, Calif. and are identical except for the orientation of the polylinker region which is reversed in one relative to the other.

The universal components of the pCMV plasmids are as follows. The vector backbone is pTZ18R (Pharmacia), and contains a bacteriophage f1 origin of replication for production of single stranded DNA and an ampicillin-resistance gene. The CMV region consists of nucleotides −760 to +3 of the powerful promoter-regulatory region of the human cytomegalovirus (Towne stain) major immediate early gene (Thonsen et al., 1984; Boshart et al., 1985). The human growth hormone fragment (hGH) contains transcription termination and poly-adenylation signals representing sequences 1533 to 2157 of this gene (Seeburg, 1982). There is an Alu middle repetitive DNA sequence in this fragment Finally, the SV40 origin of replication and early region promoter-enhancer derived from the pcD-X plasmid (HindIII to PstI fragment) described in Okayama et al., (1983). The promoter in this fragment is oriented such that transcription proceeds away from the CMV/hGH expression cassette.

The pCMV plasmids are distinguishable from each other by differences in the polylinker region and by the presence or absence of the translation enhancer. The stating pCMV1 plasmid has been progressively modified to render an increasing number of unique restriction sites in the polylinker region. To create pCMV2, one of two EcoRI sites in pCMV1 were destroyed. To create pCMV3, pCMV1 was modified by deleting a short segment from the SV40 region (StuI to EcoRI), and in so doing made unique the PstI, SalI, and BamHI sites in the polylinker. To create pCMV4, a synthetic fragment of DNA corresponding to the 5'-untranslated region of a mRNA transcribed from the CMV promoter was added C. The sequence acts as a translational enhancer by decreasing the requirements for initiation factors in polypeptide synthesis (Jobling et al., 1987; Browning et al., 1988). To create pCMV5, a segment of DNA (HpaI to EcoRI) was deleted from the SV40 origin region of pCMV1 to render unique all sites in the starting polylinker.

The pCMV vectors have been successfully expressed in simian COS cells, mouse L cells, CHO cells, and HeLa cells. In several side by side comparisons they have yielded 5- to 10-fold higher expression levels in COS cells than SV40-based vectors. The pCMV vectors have been used to express the LDL receptor, nuclear factor 1, $G_s$ alpha polypeptide, polypeptide phosphatase, synaptophysin, synapsin, insulin receptor, influenza hemagglutinin, androgen receptor, sterol 26-hydroxylase, steroid 17- and 21-hydroxylase, cytochrome P-450 oxidoreductase, beta-adrenergic receptor, folate receptor, cholesterol side chain cleavage enzyme, and a host of other cDNAs. It should be noted that the SV40 promoter in these plasmids can be used to express other genes such as dominant selectable markers. Finally, there is an ATG sequence in the polylinker between the HindIII and PstI sites in pCMV that can cause spurious translation initiation. This codon should be avoided if possible in expression plasmids. A paper describing the construction and use of the parenteral pCMV1 and pCMV4 vectors has been published (Anderson et al., 1989b).

IV. Transfected Cells

In yet another embodiment, the present invention provides recombinant host cells transformed or transfected with a polynucleotide that encodes a mu opioid receptor polypeptide or transcription regulatory polypeptide, as well as transgenic cells derived from those transformed or transfected cells. Preferably, recombinant host cells of the present invention are transfected with polynucleotide of SEQ ID NO:1 or SEQ ID NO:3. Means of transforming or transfecting cells with exogenous polynucleotide such as DNA molecules are well known in the art and include techniques such as calcium-phosphate- or DEAE-dextran-mediated transfection, protoplast fusion, electroporation, liposome mediated transfection, direct microinjection and adenovirus infection (Sabrook, Fritsch and Maniatis, 1989).

The most widely used method is transfection mediated by either calcium phosphate or DEAE-dextran. Although the mechanism remains obscure, it is believed that the transfected DNA enters the cytoplasm of the cell by endocytosis and is transported to the nucleus. Depending on the cell type, up to 90% of a population of cultured cells can be transfected at any one time. Because of its high efficiency, transfection mediated by calcium phosphate or DEAE-dextran is the method of choice for experiments that require transient expression of the foreign DNA in large numbers of cells. Calcium phosphate-mediated transfection is also used to establish cell lines that integrate copies of the foreign DNA, which are usually arranged in head-to-tail tandem arrays into the host cell genome.

In the protoplast fusion method, protoplasts derived from bacteria carrying high numbers of copies of a plasmid of interest are mixed directly with cultured mammalian cells. After fusion of the cell membranes (usually with polyethylene glycol), the contents of the bacteria are delivered into the cytoplasm of the mammalian cells and the plasmid DNA is transported to the nucleus. Protoplast fusion is not as efficient as transfection for many of the cell lines that are commonly used for transient expression assays, but it is useful for cell lines in which endocytosis of DNA occurs inefficiently. Protoplast fusion frequently yields multiple copies of the plasmid DNA tandemly integrated into the host chromosome.

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Liposome transfection involves encapsulation of DNA and RNA within liposomes, followed by fusion of the liposomes with the cell membrane. The mechanism of how DNA is delivered into the cell is unclear but transfection efficiencies can be as high as 90%.

Direct microinjection of a DNA molecule into nuclei has the advantage of not exposing DNA to cellular compartments such as low-pH endosomes. Microinjection is therefore used primarily as a method to establish lines of cells that carry integrated copies of the DNA of interest.

The use of adenovirus as a vector for cell transfection is well known in the art. Adenovirus vector-mediated cell transfection has been reported for various cells (Stratford-Perricaudet et al., 1992).

A transfected cell can be prokaryotic or eukaryotic. Preferably, the host cells of the invention are eukaryotic host cells. More preferably, the recombinant host cells of the invention are COS cells. Where it is of interest to produce a human mu opioid receptor polypeptides, cultured mammalian or human cells are of particular interest.

In another aspect, the recombinant host cells of the present invention are prokaryotic host cells. Preferably, the recombinant host cells of the invention are bacterial cells of the DH5a strain of *Escherichia coli*. In general, prokaryotes are preferred for the initial cloning of DNA sequences and constructing the vectors useful in the invention. For example, *E. coli* K12 strains can be particularly useful. Other microbial strains which can be used include *E. coli* B, and *E. coli* X1776 (ATCC No. 31537). These examples are, of course, intended to be illustrative rather than limiting.

Prokaryotes can also be used for expression. The aforementioned strains, as well as *E. coli* W3110 (F, λ, prototrophic, ATCC No. 273325), bacilli such as *Bacillus subtilis*, or other enterobacteriaceae such as *Salmonella typhimurium* or *Serratia Marcesceus*, and various Pseudomonas species can be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* can be transformed using pBR322, a plasmid derived from an *E. coli* species (Bolivar et al., 1977). pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own polypeptides.

Those promoters most commonly used in recombinant DNA construction include the β-lactamase (penicillinase) and lactose promoter systems (Chang et al., 1978; Itakura et al., 1977; Goeddel et al., 1979; Goeddel et al., 1980) and a tryptophan (TRP) promoter system (*EPO Appl. Publ. No. 0036776*; Siebwenlist et al., 1980). While these are the most commonly used, other microbial promoters have been discovered and utilized, and details concerning their nucleotide sequences have been published, enabling a skilled worker to introduce functional promoters into plasmid vectors (Siebwenlist et al., 1980).

In addition to prokaryotes, eukaryotic microbes, such as yeast can also be used. *Saccharomyces cerevisiae* or common baker's yeast is the most commonly used among eukaryotic microorganisms, although a number of other strains are commonly available. For expression in Saccharomyces, the plasmid YRp7, for example, is commonly used (Stinchcomb et al., 1979; Kingsman et al., 1979; Tschemper et al., 1980). This plasmid already contains the trpl gene which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoter sequences in yeast vectors include the promoters for 3-phosphoglycerate kinase (Hitzeman et al., 1980) or other glycolytic enzymes (Hess et al., 1968; Holland et al., 1978) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also introduced into the expression vector downstream from the sequences to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utlization Any plasmid vector containing a yeast-compatible promoter, origin or replication and termination sequences is suitable.

In addition to microorganisms, cultures of cells derived from multicellular organisms can also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (Kruse and Peterson, 1973). Examples of such useful host cell lines are AtT-20, VERO and HeLa cells, Chinese hamster ovary (CHO) cell lines, and W138, BHK, COSM6, COS-1, COS-7, 293 and MDCK cell lines. Expression vectors for such cells ordinarily include (if necessary) an origin of replication, a promoter located upstream of the gene to be expressed, along with any necessary ribosome binding sites, RNA splice sites, polyadenylation site, and transcriptional terminator sequences.

For use in mammalian cells, the control functions on the expression vectors are often derived from viral material. For example, commonly used promoters are derived from polyoma, Adenovinrus 2, Cytomegalovirus and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments can also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication can be provided with by construction of the vector to include an exogenous origin, such as can be derived from SV40 or other viral (e.g., Polyoma, Adeno, VSV, BPV, CMV) source, or can be provided by the host cell chromosomal replication mechanism. If the vector is integrated into the host cell chromosome, the latter is often sufficient.

V. Preparing a Recombinant Mu Opioid Receptor Polypeptide or Transcription Regulatory Polypeptide In yet another embodiment, the present invention contemplates a process of preparing a mu opioid receptor polypeptide comprising transfecting cells with a polynucleotide that encodes a mu opioid receptor polypeptide to produce transformed host cells; and maintaining the transformed host cells under biological conditions sufficient for expression of the polypeptide. Preferably, the transformed host cells are eukaryotic cells. More preferably still, the eukaryotic cells are COS cells. Alternatively, the host cells are prokaryotic cells. More preferably, the prokaryotic cells are bacterial cells of the DH5α strain of *Escherichia coli*. Even more preferably, the polynucleotide transfected into the transformed cells comprise the nucleotide base sequence of SEQ ID NO:1. Most preferably, transfection is accomplished using a hereinbefore disclosed expression vector.

In yet another embodiment, the present invention contemplates a process of preparing a gene transcript comprising transfecting cells with a polynucleotide that encodes a gene transcription regulatory polypeptide to produce transformed host cells; and maintaining the transformed host cells under biological conditions sufficient for expression of the polypeptide. Preferably, the transformed host cells are eukaryotic cells. More preferably still, the eukaryotic cells are COS cells. Alternatively, the host cells are prokaryotic cells. More preferably, the prokaryotic cells are bacterial cells of the DH5α strain of *Escherichia coli*. Even more preferably, the polynucleotide transfected into the transformed cells comprise the nucleotide base sequence of SEQ ID NO:3. Most preferably transfection is accomplished using a hereinbefore disclosed expression vector.

A host cell used in the process is capable of expressing a functional, recombinant mu opioid receptor polypeptide. A preferred host cell is a Chinese hamster ovary cell. However, a variety of cells are amenable to a process of the invention, for instance, yeasts cells, human cell lines, and other eukaryotic cell lines known well to those of the art.

Following transfection, the cell is maintained under culture conditions for a period of time sufficient for expression of a mu opioid receptor polypeptide. Culture conditions are well known in the art and include ionic composition and concentration, temperature, pH and the like. Typically, transfected cells are maintained under culture conditions in a culture medium Suitable medium for various cell types are well known in the art. In a preferred embodiment, temperature is from about 20° C. to about 50° C., more preferably from about 30° C. to about 40° C. and, even more preferably about 37° C.

pH is preferably from about a value of 6.0 to a value of about 8.0, more preferably from about a value of about 6.8 to a value of about 7.8 and, most preferably about 7.4. Osmolality is preferably from about 200 milliosmols per liter (mosm/L) to about 400 mosm/l and, more preferably from about 290 mosm/L to about 310 mosm/L. Other biological conditions needed for transfection and expression of an encoded protein are well known in the art.

Transfected cells are maintained for a period of time sufficient for expression of a mu opioid receptor polypeptide. A suitable time depends inter alia upon the cell type used and is readily determinable by a skilled artisan. Typically, maintenance time is from about 2 to about 14 days.

A recombinant mu opioid receptor polypeptide or gene transcription regulatory polypeptide is recovered or collected either from the transfected cells or the medium in which those cells are cultured. Recovery comprises isolating and purifying the recombinant polypeptide. Isolation and purification techniques for polypeptides are well known in the art and include such procedures as precipitation, filtration, chromatography, electrophoresis and the like.

VI. Antibodies

In still another embodiment, the present invention provides antibodies immunoreactive with a polypeptide of the present invention. Preferably, the antibodies of the invention are monoclonal antibodies. More preferably, the polypeptide comprises the amino acid residue sequence of SEQ ID NO:2 or SEQ ID NO:4. Means for preparing and characterizing antibodies are well known in the art (See, eg., Harlow E. and D. Lane, 1988).

Briefly, a polyclonal antibody is prepared by immunizing an animal with an immunogen comprising a polypeptide or polynucleotide of the present invention, and collecting antisera from that immunized animal. A wide range of animal species can be used for the production of antisera Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide or polynucleotide may vary in its immunogenicity. It is often necessary therefore to couple the immunogen (e.g., a polypeptide or polynucleotide) of the present invention) with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Means for conjugating a polypeptide or a polynucleotide to a carrier protein are well known in the art and include glutaraldehyde, M maleimidobenzoyl-N-hydroxysuccinimide ester, carbodiimide and bis-biazotized benzidine.

As is also well known in the art, immunogencity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies inter alia, upon the nature of the immunogen as well as the animal used for immunization. A variety of routes can be used to administer the immunogen (subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal can be bled and the serum isolated and stored.

In another aspect, the present invention contemplates a process of producing an antibody immunoreactive with a mu opioid receptor polypeptide comprising the steps of (a) transfecting recombinant host cells with polynucleotide that encodes a mu opioid receptor polypeptide; (b) culturing the host cells under conditions sufficient for expression of the polypeptide; (c) recovering the polypeptide; and (d) preparing the antibodies to the polypeptide. Preferably, the host cell is transfected with the polynucleotide of SEQ ID NO:1 or SEQ ID NO:3. Even more preferably, the present invention provides antibodies prepared according to the process described above.

A monoclonal antibody of the present invention can be readily prepared through use of well-known techniques such as those exemplified in U.S. Pat. No 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microliter plates, followed by testing the individual clonal supernatants for reactivity with an antigen-polypeptides. The selected clones can then be propagated indefinitely to provide the monoclonal antibody.

By way of specific example, to produce an antibody of the present invention, mice are injected intraperitoneally with between about 1–200 μg of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radio-labeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The bybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immuno-specific reaction with the bound antibody. The polypeptide or polynucleotide is then easily removed from the substrate and purified.

VII. Pharmaceutical Compositions

In a preferred embodiment, the present invention provides pharmaceutical compositions comprising a mu opioid receptor polypeptide or a gene transcription regulatory polypeptide and a physiologically acceptable carrier. More preferably, a pharmaceutical composition comprises a mu opioid receptor polypeptide having the amino acid residue sequence of SEQ ID NO:2 or SEQ ID NO:4. Even more preferably, a pharmaceutical composition of the invention comprises a polynucleotide that encodes a mu opioid receptor polypeptide and a physiologically acceptable carrier. Still more preferably, a pharmaceutical composition of the present invention comprises the amino acid residue sequence of SEQ ID NO:2 or SEQ ID NO:4. Alternatively, a pharmaceutical composition comprises the nucleotide sequence of SEQ ID NO:1 or SEQ ID NO:3.

A composition of the present invention is typically administered parenterally in dosage unit formulations containing standard, well-known nontoxic physiologically acceptable carriers, adjuvants, and vehicles as desired. The term parenteral as used herein includes intravenous, intramuscular, intraarterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminants, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A carrier can also be a liposome. Means for using liposomes as delivery vehicles are well known in the art [See, e.g. Gabizon, et al., 1990; Ferruti, et al., 1986; and Ranade, 1989].

A transfected cell can also serve as a carrier. By way of example, a liver cell can be removed from an organism, transfected with a polynucleotide of the present invention using methods set forth above and then the transfected cell returned to the organism (e.g. injected intravascularly).

VIII. A Process of Detecting Polynucleotide and the Polypeptides Encoded

Alternatively, the present invention provides a process of detecting a polypeptide of the present invention, wherein the process comprises immunoreacting the polypeptide with antibodies prepared according to a process described above to form an antibody-polypeptide conjugate and detecting the conjugates.

In yet another embodiment, the present invention contemplates a process of detecting a messenger RNA transcript that encodes a mu opioid receptor polypeptide or a gene transcription regulatory polypeptide, wherein the process comprises (a) hybridizing the messenger RNA transcript with a polynucleotide sequence that encodes the polypeptide to form a duplex; and (b) detecting the duplex. Alternatively, the present invention provides a process of detecting a DNA molecule that encodes a mu opioid receptor polypeptide, wherein the process comprises (a) hybridizing DNA molecules with a polynucleotide that encodes a mu opioid receptor polypeptide to form a duplex; and (b) detecting the duplex.

IX. Screening Assays

In yet another aspect, the present invention contemplates a process of screening substances for their ability to interact with a mu opioid receptor polypeptide or a gene transcription regulatory polypeptide, the process comprising the steps of providing a polypeptide of the present invention and testing the ability of selected substances to interact with that polypeptide.

Utilizing the methods and compositions of the present invention, screening assays for the testing of candidate substances such as agonists and antagonists of mu opioid receptors can be derived. A candidate substance is a substance which can interact with or modulate, by binding or other intramolecular interaction, a mu opioid receptor polypeptide or a gene transcription regulatory polypeptide. In some instances, such a candidate substance is an agonist of the receptor and in other instances can exhibit antagonistic attributes when interacting with the receptor polypeptide. In other instances, such substances have mixed agonistic and antagonistic properties or can modulate the receptor in other ways. Alternatively, such substances can promote or inhibit transcription of a mu opioid receptor.

Recombinant receptor expression systems of the present invention possess definite advantages over tissue-based systems. The methods of the present invention make it possible to produce large quantities of mu opioid receptors for use in screening assays. More important, however, is the relative purity of the receptor polypeptides provided by the present invention. A relatively pure polypeptide preparation for assaying a protein-protein interaction makes it possible to use elutive methods without invoking competing, and unwanted, side-reactions.

Cloned expression systems such as those of the present invention are also useful where there is difficulty in obtaining tissue that satisfactorily expresses a particular receptor. Cost is another very real advantage, at least with regard to the microbial expression systems of the present invention. For antagonists in a primary screen, microorganism expression systems of the present invention are inexpensive in comparison to prior art tissue-screening methods.

Traditionally, screening assays employed the use of crude receptor preparations. Typically, animal tissue slices thought to be rich in the receptor of interest were the source of the receptor. Alternatively, investigators homogenized the tissue and used the crude homogenate as a receptor source. A major difficulty with this approach is that there are no tissue types where only one receptor type is expressed. The data obtained therefore could not be definitively correlated with a particular receptor. With the recent cloning of receptor sub-types and sub-sub-types, this difficulty is highlighted. A second fundamental difficulty with the traditional approach is the unavailability of human tissue for screening potential drugs. The traditional approach almost invariably utilized animal receptors. With the cloning of human receptors, there is a need for screening assays which utilize human receptors.

With the availability of cloned receptors, recombinant receptor screening systems have several advantages over tissue based systems. A major advantage is that the investigator can now control the type of receptor that is utilized in a screening assay. Specific receptor sub-types and sub-sub-types can be preferentially expressed and its interaction with a ligand can be identified. Other advantages include the availability of large amounts of receptor, the availability of rare receptors previously unavailable in tissue samples, and the lack of expenses associated with the maintenance of live animals.

Screening assays of the present invention generally involve determining the ability of a candidate substance to bind to the receptor and to affect the activity of the receptor, such as the screening of candidate substances to identify those that inhibit or otherwise modify the receptor's function. Typically, this method includes preparing recombinant receptor polypeptide, followed by testing the recombinant polypeptide or cells expressing the polypeptide with a candidate substance to determine the ability of the substance to affect its physiological function. In preferred embodiments, the invention relates to the screening of candidate substances to identify those that affect the enzymatic activity of the human receptor, and thus can be suitable for use in humans.

As is well known in the art, a screening assay provides a receptor under conditions suitable for the binding of an agent to the receptor. These conditions include but are not limited to pH, temperature, tonicity, the presence of relevant co-factors, and relevant modifications to the polypeptide such as glycosylation or prenylation. It is contemplated that the receptor can be expressed and utilized in a prokaxyotic or eukaryotic cell. The host cell expressing the receptor can be used whole or the receptor can be isolated from the host cell. The receptor can be membrane bound in the membrane of the host cell or it can be free in the cytosol of the host cell The host cell can also be fractionated into sub-cellular fractions where the receptor can be found. For example, cells expressing the receptor can be fractionated into the nuclei, the endoplasmic reticulum, vesicles, or the membrane surfaces of the cell.

pH is preferably from about a value of 6.0 to a value of about 8.0, more preferably from about a value of about 6.8 to a value of about 7.8 and, most preferably about 7.4. In a preferred embodiment, temperature is from about 20° C. to about 50° C., more preferably from about 30° C. to about 40° C. and, even more preferably about 37° C. Osmolality is preferably from about 5 milliosmols per liter (mosm/L) to about 400 mosm/L and, more preferably from about 200 milliosmols per liter to about 400 mosm/L and, even more preferably from about 290 mosm/L to about 310 mosm/L. The presence of co-factors can be required for the proper functioning of the receptor. Typical co-factors include sodium, potassium, calcium, magnesium, and chloride. In addition, small, non-peptide molecules, known as prosthetic groups can be required. Other biological conditions needed for receptor function are well known in the art.

It is well known in the art that proteins can be reconstituted in artificial membranes, vesicles or liposomes. (Danboldt et al., 1990). The present invention contemplates that the receptor can be incorporated into artificial membranes, vesicles or liposomes. The reconstituted receptor can be utilized in screening assays.

It is further contemplated that the receptor of the present invention can be coupled to a solid support. The solid support can be agarose beads, polyacrylamide beads, polyacrylic beads or other solid matrices capable of being coupled to proteins. Well known coupling agents include cyanogen bromide, carbonyidiimidazole, tosyl chloride, and glutaraldehyde.

It is further contemplated that secondary polypeptides which can function in conjunction with the receptor of the present invention can be provided. For example, the receptor of the present invention exerts its physiological effects in conjunction with a G-protein and an effector polypeptide.

In a typical screening assay for identifying candidate substances, one employs the same recombinant expression host as the starting source for obtaining the receptor polypeptide, generally prepared in the form of a crude homogenate. Recombinant cells expressing the receptor are washed and homogenized to prepare a crude polypeptide homogenate in a desirable buffer such as disclosed herein. In a typical assay, an amount of polypeptide from the cell homogenate, is placed into a small volume of an appropriate assay buffer at an appropriate pH. Candidate substances, such as agonists and antagonists, are added to the admixture in convenient concentrations and the interaction between the candidate substance and the receptor polypeptide is monitored.

Where one uses an appropriate known substrate for the receptor, one can, in the foregoing manner, obtain a baseline activity for the recombinantly produced receptor. Then, to test for inhibitors or modifiers of the receptor function, one can incorporate into the admixture a candidate substance whose effect on the receptor is unknown. By comparing reactions which are carried out in the presence or absence of the candidate substance, one can then obtain information regarding the effect of the candidate substance on the normal function of the receptor.

Accordingly, it is proposed that this aspect of the present invention provides those of skill in the art with methodology that allows for the identification of candidate substances having the ability to modify the action of opioid receptor polypeptides in one or more manners.

In one embodiment, such an assay is designed to be capable of discriminating those candidate substances with the desirable properties of opioids but which lack the undesirable properties of opioids. In another embodiment, screening assays for testing candidate substances such as agonists and antagonists of mu opioid receptors are used to identify such candidate substances having selective ability to interact with one or more of the opioid receptor polypeptides but which polypeptides are without a substantially overlapping activity with other opioid receptors.

Additionally, screening assays for the testing of candidate substances are designed to allow the investigation of structure activity relationships of opioids with the mu receptors, e.g., study of binding of naturally occurring hormones or other substances capable of interacting or otherwise modulating with the mu receptor versus studies of the activity caused by the binding of such molecules to the mu receptor. In certain embodiments, the polypeptides of the invention are crystallized in order to carry out x-ray crystallographic studies as a means of evaluating interactions with candidate substances or other molecules with the opioid receptor polypeptide. For instance, the purified recombinant polypeptides of the invention, when crystallized in a suitable form, are amenable to detection of intra-molecular interactions by x-ray crystallography.

An important aspect of the invention is the use of recombinantly produced mu opioid receptor polypeptide in screening assays for the identification of substances which can inhibit or otherwise modify or alter the function of the receptor. The use of recombinantly produced receptor is of particular benefit because the naturally occurring receptor is present in only small quantities and has proven difficult to purify. Moreover, this provides a ready source of receptor, which has heretofore been unavailable.

As described above, receptors in the presence of agonists can exert their physiological effects through a secondary molecule. A screening assay of the invention, in preferred embodiments, conveniently employs a mu opioid receptor polypeptide directly from the recombinant host in which it is produced. This is achieved most preferably by simply expressing the selected polypeptide within the recombinant host, typically a eukaryotic host, followed by preparing a crude homogenate which includes the polypeptide. A portion of the crude homogenate is then admixed with an appropriate effector of the mu receptor along with the candidate substance to be tested. By comparing the binding of the selected effector to the receptor in the presence or absence of the candidate substance, one can obtain information regarding the physiological properties of the candidate substance.

The receptor can be expressed in a prokaryotic or a eukaryotic cell. Receptors have been expressed in *E. coli* (Bertin et al., 1992), in yeast (King et al., (1990) and in mammalian cells (Bouvier et. al. 1988).

A cell expressing a receptor can be used whole to screen agents. For example, cells expressing the receptor of the present invention can be exposed to radiolabelled agent and the amount of binding of the radiolabelled agent to the cell can be determined.

The cell expressing the receptor can be fractionated into sub-cellular components which contain the receptor of the present invention. Methods for purifying sub-cellular fractions are well known in the art. Sub-cellular fractions include but are not limited to the cytoplasm, cellular membrane, other membranous fractions such as the endoplasmic reticulum, golgi bodies, vesicles and the nucleus. Receptors isolated as sub-cellular fractions can be associated with cellular membranes. For example, if cellular membrane vesicles are isolated from the cell expressing the receptor, the receptor molecule can be membrane bound. It is further contemplated that the receptor of the present invention can be purified from a cell that expresses the receptor. Methods of purification are well known in the art. The purified receptor can be used in screening assays.

In that most such screening assays in accordance with the invention are designed to identify agents useful in mimicking the desirable aspects of opioids while eliminating the undesirable aspects of the hormone, preferred assays employ opioids as the normal agonist.

There are believed to be a wide variety of embodiments that can be employed to determine the effect of the candidate substance on a mu receptor polypeptide of the invention, and the invention is not intended to be limited to any one such method. However, it is generally desirable to employ a system wherein one can measure the ability of the receptor polypeptide to bind to and or be modified by the effector employed in the presence of a particular substance.

The detection of an interaction between an agent and a receptor can be accomplished through techniques well known in the art. These techniques include but are not limited to centrifugation, chromatography, electrophoresis and spectroscopy. The use of isotopically labelled reagents in conjunction with these techniques or alone is also contemplated. Commonly used radioactive isotopes include $^3$H, $^{14}$C, $^{22}$Na, $^{32}$P, $^{35}$S, $^{45}$Ca. $^{60}$Co, $^{125}$I, and $^{131}$I. Commonly used stable isotopes include $^2$H, $^{13}$C, $^{15}$N, $^{18}$O.

For example, if an agent can bind to the receptor of the present invention, the binding can be detected by using radiolabeled agent or radiolabeled receptor. Briefly, if radiolabeled agent or radiolabeled receptor is utilized, the agent-receptor complex can be detected by liquid scintillation or by exposure to X-Ray film.

The interaction of an agent and a receptor can also be detected by the use of atomic force microscopy (AFM). Three dimensional images of biological materials (e.g. proteins, nucleic acids and membranes) under physiological conditions can be obtained with nanometer resolution through AFM. AFM has been used to image a number of biological specimens. (Edstrom et al.,, 1990; Drake et al., 1989; Butt et al., 1990; Hoh et al., 1991; Weisenhom et al., 1990; Henderson et al., 1992; Hansma et al., 1992; Durbin, S. D. and W. E. Carlson, 1992; and Lal et al., 1993).

AFM operates by measuring the atomic force between the tip of an AFM probe and the top surface of the sample being imaged. The probe used for AFM is an integral part of a micro-fabricated cantilever, often made of $Si_3N_4$. AFM senses height of the sample surface and controls the vertical position of the sample by tracking the deflection of the cantilever. The position of the cantilever is monitored via laser beam reflection off the cantilever to an optical position sensor. The signal is used in a feedback mechanism to control the height of the sample. This feedback mechanism allows the AFM to scan over the sample surface at a constant deflection, hence a constant force. Because the atomic force is a function of inter-atomic distance, the height position of the probe represents the sample surface contour. The vertical features of the sample are thus recorded as the probe is moved over the surface in a horizontal raster scan, and the image of the sample surface can be displayed in real time during imaging and analyzed at a later time.

Recently, the cloned nicotinic acetylcholine receptor expressed in *Xenopus oocytes* was imaged by AFM by the present inventor. The AFM image revealed that the acetylcholine receptor was roughly 13 nm, traversing the lipid bilayer and protruding a few nanometers out of the plasma membrane and into the cytoplasm The AFM image also showed that the acetylcholine receptors clustered together in the lipid bilayer. The average distance between individual receptors in Xenopus oocytes was roughly 9–11 nm.

The interaction of an agonist or an antagonist with a mu opioid receptor can be imaged by AFM. The characterization of intermolecular arrangements and interactions, such as ligand-receptor, antibody-receptor, antibody-transcription regulatory peptide can be achieved by AFM.

When an agent modifies the receptor, the modified receptor can also be detected by differences in mobility between the modified receptor and the unmodified receptor through the use of chromatography, electrophoresis or centrifugation. When the technique utilized is centrifugation, differences in mobility are known as the sedimentation coefficient. The modification can also be detected by differences between the spectroscopic properties of the modified and unmodified receptor. As a specific example, if an agent covalently modifies a receptor, the difference in retention times between modified and unmodified receptor on a high pressure liquid chromatography (HPLC) column can easily be detected.

As a specific example, where an agent covalently modifies a receptor, the spectroscopic differences between modified and unmodified receptor in the nuclear magnetic resonance (NMR) spectra can be detected. Alternatively, one can focus on the agent and detect the differences in the spectroscopic properties or the difference in mobility between the free agent and the agent after modification of the receptor.

Where a secondary polypeptide is provided, the agent-receptor-secondary polypeptide complex or the receptor-secondary polypeptide complex can be detected. Differences in mobility or differences in spectroscopic properties as described above can be detected.

It is further contemplated that where a secondary polypeptide is provided the enzymatic activity of the effector polypeptide can be detected. For example, many receptors exert physiological effects through the stimulation or inhibition of adenylyl cyclase. The enzymatic activity of adenylyl cyclase in the presence of an agent can be detected.

The interaction of an agent and a receptor can be detected by providing a reporter gene. Well known reporter genes include β-galactosidase (β-Gal), chloramphenicol transferase (CAT) and luciferase. The reporter gene is expressed by the host and the enzymatic reaction of the reporter gene product can be detected.

In preferred assays, an admixture containing the polypeptide, effector and candidate substance is allowed to incubate for a selected amount of time, and the resultant incubated mixture subjected to a separation means to separate the unbound effector remaining in the admixture from any effector/receptor complex so produced. Then, one simply measures the amount of each (e.g., versus a control to which no candidate substance has been added). This measurement can be made at various time points where velocity data is desired. From this, one can determine the ability of the candidate substance to alter or modify the function of the receptor.

Numerous techniques are known for separating the effector from effector/receptor complex, and all such methods are intended to fall within the scope of the invention. Use of thin layer chromatographic methods (TLC), HPLC, spectrophotometric, gas chromatographic/mass spectrophotometric or NMR analyses. It is contemplated that any such technique can be employed so long as it is capable of differentiating between the effector and complex, and can be used to determine enzymatic function such as by identifying or quantifying the substrate and product.

The effector/receptor complex itself can also be the subject of techniques such as x-ray crystallography. Where a candidate substance replaces the opioid molecule as the drug's mode of action, studies designed to monitor the replacement and its effect on the receptor will be of particular benefit.

A. Screening Assays for mu Opioid Receptor Polypeptides

The present invention provides a process of screening a biological sample for the presence of a mu opioid receptor polypeptide. A biological sample to be screened can be a biological fluid such as extracellular or intracellular fluid or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide.

In accordance with a screening assay process, a biological sample is exposed to an antibody immunoreactive with the mu opioid receptor polypeptide whose presence is being assayed. Typically, exposure is accomplished by forming an admixture in a liquid medium that contains both the antibody and the candidate opioid receptor polypeptide. Either the antibody or the sample with the opioid receptor polypeptide can be affixed to a solid support (e.g., a column or a microliter plate).

The biological sample is exposed to the antibody under biological reaction conditions and for a period of time sufficient for antibody-polypeptide conjugate formation. Biological reaction conditions include ionic composition and concentration, temperature, pH and the like.

Ionic composition and concentration can range from that of distilled water to a 2 molal solution of NaCl. Preferably, osmolality is from about 100 mosmols/l to about 400 mosmols/l and, more preferably from about 200 mosmols/l to about 300 mosmols/l. Temperature preferably is from about 4° C. to about 100° C., more preferably from about 15° C. to about 50° C. and, even more preferably from about 25° C. to about 40° C. pH is preferably from about a value of 4.0 to a value of about 9.0, more preferably from about a value of 6.5 to a value of about 8.5 and, even more preferably from about a value of 7.0 to a value of about 7.5. The only limit on biological reaction conditions is that the conditions selected allow for antibody-polypeptide conjugate formation and that the conditions do not adversely affect either the antibody or the opioid receptor polypeptide.

Exposure time will vary inter alia with the biological conditions used, the concentration of antibody and polypeptide and the nature of the sample (e.g., fluid or tissue sample). Means for determining exposure time are well known to one of ordinary skill in the art. Typically, where the sample is fluid and the concentration of polypeptide in that sample is about $10^{-10}$ M, exposure time is from about 10 minutes to about 200 minutes.

The presence of mu opioid receptor polypeptide in the sample is detected by detecting the formation and presence of antibody-mu opioid receptor polypeptide conjugates. Means for detecting such antibody-antigen (e.g., receptor polypeptide) conjugates or complexes are well S known in the art and include such procedures as centrifugation, affinity chromatography and the like, binding of a secondary antibody to the antibody-candidate receptor complex.

In one embodiment, detection is accomplished by detecting an indicator affixed to the antibody. Exemplary and well known such indicators include radioactive labels (e.g., $^{32}$P, $^{125}$I, $^{14}$C), a second antibody or an enzyme such as horse radish peroxidase. Means for affixing indicators to antibodies are well known in the art. Commercial kits are available.

B. Screening Assay for Anti-mu Opioid Receptor Antibody

In another aspect, the present invention provides a process of screening a biological sample for the presence of antibodies immunoreactive with a mu opioid receptor polypeptide (i.e., an anti-mu opioid receptor antibody). In accordance with such a process, a biological sample is exposed to a mu opioid receptor polypeptide under biological conditions and for a period of time sufficient for antibody-polypeptide conjugate formation and the formed conjugates are detected.

C. Screening Assay for a Polynucleotide that Encodes a mu Opioid Receptor Polypeptide A DNA molecule and, particularly a probe molecule, can be used for hybridizing as oligonucleotide probes to a DNA source suspected of possessing a mu opioid receptor polypeptide encoding polynucleotide or gene. The probing is usually accomplished by hybridizing the oligonucleotide to a DNA source suspected of possessing such a receptor gene. In some cases, the probes constitute only a single probe, and in others, the probes constitute a collection of probes based on a certain amino acid sequence or sequences of the opioid receptor polypeptide and account in their diversity for the redundancy inherent in the genetic code.

A suitable source of DNA for probing in this manner is capable of expressing mu opioid receptor polypeptides and can be a genomic library of a cell line of interest. Alternatively, a source of DNA can include total DNA from the cell line of interest. Once the hybridization process of the invention has identified a candidate DNA segment, one confirms that a positive clone h as been obtained by further hybridization, restriction enzyme mapping, sequencing and/or expression and testing.

Alternatively, such DNA molecules can be used in a number of techniques including their use as: (1) diagnostic tools to detect normal and abnormal DNA sequences in DNA derived from patient's cells; (2) means for detecting and isolating other members of the opioid receptor family and related polypeptides from a DNA library potentially containing such sequences; (3) primers for hybridizing to related sequences for the purpose of amplifying those sequences; (4) primers for altering the native opioid receptor DNA sequences; as well as other techniques which rely on the similarity of the DNA sequences to those of the opioid receptor DNA segments herein disclosed.

As set forth above, in certain aspects, DNA sequence information provided by the invention allows for the preparation of relatively short DNA (or RNA) sequences (e.g., probes) that specifically hybridize to encoding sequences of the selected opioid receptor gene. In these aspects, nucleic acid probes of an appropriate length are prepared based on a consideration of the selected opioid receptor sequence (e.g., a sequence such as that shown in SEQ ID NO:1 or SEQ ID NO:3. The ability of such nucleic acid probes to specifically hybridize to mu opioid receptor encoding sequences lend them particular utility in a variety of embodiments. Most importantly, the probes can be used in a variety of assays for detecting the presence of complementary sequences in a given sample. However, uses are envisioned, including the use of the sequence information for the preparation of mutant species primers, or primers for use in preparing other genetic constructions.

To provide certain of the advantages in accordance with the invention, a preferred nucleic acid sequence employed for hybridization studies or assays includes probe sequences that are complementary to at least a 14 to 40 or so long nucleotide stretch of the mu opioid receptor encoding sequence, such as that shown in SEQ ID NO:1 and SEQ ID NO:3. A size of at least 14 nucleotides in length helps to ensure that the fragment is of sufficient length to form a duplex molecule that is both stable and selective. Molecules having complementary sequences over stretches greater than 14 bases in length are generally preferred, though, to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Such fragments can be readily prepared by, for example, directly synthesizing the fragment by chemical means, by application of nucleic acid reproduction technology, such as the PCR™ technology of U.S. Pat. No. 4,683,202, herein incorporated by reference, or by introducing selected sequences into recombinant vectors for recombinant production.

Accordingly, a nucleotide sequence of the present invention can be used for its ability to selectively form duplex molecules with complementary stretches of the gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by 0.02M–0.15M NaCl at temperatures of 50° C. to 70° C. Such conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate opioid receptor coding sequences from related species, functional equivalents, or the like, less stringent hybridization conditions are typically needed to allow formation of the heteroduplex. Under such circumstances, one employs conditions such as 0.15M–0.9M salt, at temperatures ranging from 20° C. to 70° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a nucleic acid sequence of the present invention in combination with an appropriate means, such as a label, for determining hybridization A wide variety of appropriate indicator means are known in the art, including radioactive, enzymatic or other ligands, such as avidin/biotin, which are capable of giving a detectable signal. In preferred embodiments, one likely employs an enzyme tag such a urease, alkaline phosphatase or peroxidase, instead of radioactive or other environmentally undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein are useful both as reagents in solution hybridization as well as in embodiments employing a solid phase. In embodiments involving a solid phase, the sample containing test DNA (or RNA) is adsorbed or otherwise affixed to a selected matrix or surface. This fixed, single-stranded nucleic acid is then subjected to specific hybridization with selected probes under desired conditions. The selected conditions depend inter alia on the particular circumstances based on the particular criteria required (depending, for example, on the G+C contents type of target nucleic acid, source of nucleic acid, size of hybridization probe, etc.). Following washing of the hybridized surface so as to remove non-specifically bound probe molecules, specific hybridization is detected, or even quantified, by means of the label.

D. Screening For Agonists and Antagonists

Mu receptors are one of the major subtypes of opioid receptors. Therefore, highly selective mu opioid receptor agonists are clinically useful.

Development of highly selective, clinically useful mu opioid receptor agonists is facilitated by understanding the specific sites within the mu receptor necessary for agonist binding. The recent cloning of the rodent mu opioid receptor cDNA has opened up the possibility to investigate the structural domains of this receptor subtype that are responsible for its functioning.

X. Assay Kits

In another aspect, the present invention contemplates diagnostic assay kits for detecting the presence of mu opioid receptor polypeptides in biological samples, where the kits comprise a first container containing a first antibody capable of immunoreacting with mu opioid receptor polypeptides, with the first antibody present in an amount sufficient to perform at least one assay. Preferably, assay kits of the invention further comprise a second container containing a second antibody that immunoreacts with the first antibody. Preferably the antibodies used in the assay kits of the present invention are monoclonal antibodies. Even more preferably, the first antibody is affixed to a solid support. More preferably still, the first and second antibodies comprise an indicator, and, preferably, the indicator is a radioactive label or an enzyme.

The present invention also contemplates a diagnostic kit for screening agents. Such a kit comprises a mu opioid receptor of the present invention. The kit can further contain reagents for detecting an interaction between an agent and a receptor of the present invention. The provided reagent can be radiolabeled. The kit can contain a known radiolabeled agent capable of binding or interacting with a receptor of the present invention.

It is further contemplated that the kit can contain a secondary polypeptide. The secondary polypeptide can be a G-protein. The secondary polypeptide can also be an effector protein. When a secondary polypeptide is included in a kit, reagents for detecting an interaction between the receptor and the secondary polypeptide can be provided. As a specific example, an antibody capable of detecting a receptor/G-protein complex can be provided. As another specific example, an antibody capable of detecting a G-protein/effector complex can be provided. Reagents for the detection of the effector can be provided. For example, if the effector provided is adenylyl cyclase, reagents for detecting the activity of adenylyl cyclase can be provided. The identity of such agents is within the knowledge of those skilled in the relevant art.

In an alternative aspect, the present invention provides diagnostic assay kits for detecting the presence, in biological samples, of a polynucleotide that encodes a mu opioid receptor polypeptides, the kits comprising a first container that contains a second polynucleotide identical or complementary to a segment of at least 10 contiguous nucleotide bases of SEQ ID NO:1 or SEQ ID NO:3.

In another embodiment, the present invention contemplates diagnostic assay kits for detecting the presence, in a biological sample, of antibodies immunoreactive with mu opioid receptor polypeptides, the kits comprising a first container containing a mu opioid receptor polypeptide that immunoreacts with the antibodies, with the polypeptides present in an amount sufficient to perform at least one assay. The reagents of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media or a microscope slide. When the reagent provided is a dry powder, the powder can be reconstituted by the addition of a suitable solvent. The solvent can be provided.

EXAMPLES

Examples are included to illustrate preferred modes of the invention. Certain aspects of the following examples are described in terms of techniques and procedures found or contemplated by the present inventors to work well in the practice of the invention. These examples are exemplified through the use of standard laboratory practices of the inventor. In light of the present disclosure and the general level of skill in the art, those of skill will appreciate that the following examples are intended to be exemplary only and that numerous changes, modifications and alterations can be employed without departing from the spirit and scope of the invention.

Example I
Isolation of cDNA Clones

Low stringency hybridization was utilized for isolating opioid receptors related to the mouse δ-opioid receptor (Evan et al., 1992; Kieffer et al., 1992) because all three types of opioid receptors share sequence homology, share overlapping pharmacology, couple to G proteins, and have a common effect on $Ca^{2+}$ and $K^+$ channels (Pastrenak G. W. 1988). Oligodeoxynucleotides were synthesized based on the mouse δ-opioid receptor sequence (Evan et al., 1992 and Kieffer et al., 1992) and were used to amplify, by PCR, a sequence fragment from a rat brain cDNA library (Snutch et al., 1990).

Two primers, ATCTTCACCCTCACCATGATG (SEQ. ID. NO:5) and CGGTCCITCTCCTTGGAACC (SEQ. ID. NO:6), were synthesized from the sequence of the mouse δ-opioid receptor (Evans et al., 1992; Kieffer et al., 1992), corresponding to the third transmembrane domain and the third cytoplasmic loop, respectively. PCR™ was performed using purified DNA from a rat brain cDNA library (Snutch et al., 1990), in an air Thermo-cycler (Idaho Technology) under modified conditions (94° for 10 sec, 56° for 20 sec, and 72° for 40 sec, for 40 cycles). A 356 bp fragment was purified and subcloned into pBLUESCRIPT SK(+) vector. Sequence analysis of the resulting 356 bp PCR™ product revealed complete identity with the corresponding portion of the δ-opioid receptor (Evans et al., 1992), showing a conserved relationship between the δ-opioid receptors from these two species.

The 356-bp fragment was then used to screen a rat brain cDNA library under low stringency conditions (6×SSPE (1.08M NaCl, 60 mM $NaH_2PO_4$, 6 mM EDTA, pH 7.4), 5× Denhardt solution, 0.5% sodium dodecyl sulfate, 100 μg/ml salmon sperm DNA, at 50°). The final wash was carried out in 0.5× standard saline citrate (7 mM NaCl, 7.5 mM sodium citrate), 0.1% sodium dodecyl sulfate, at 50° C. Phagemids were rescued from positive λ clones by infection with helper phage. Two independent isolates were used for sequence determination by shotgun cloning into pBLUESCRIPT SK(+). Subsequent sequencing of both strands from each isolate showed these two clones to be identical. Potential post-translational modification sites were identified by using the PCGENE program. Comparison of the sequence with other receptors was performed by using the BLAST program (National Institutes of Health).

Sequence analysis revealed that one cDNA clone contained an open reading frame of 1194 bp, encoding a protein of 398 amino acids. Hydropathy analysis of the deduced protein indicated seven hydrophobic domains, typical of G protein-coupled receptors (Collins et al., 1991). This protein, termed MOR-1, shows high levels of homology with the mouse δ-opioid receptor DOR-1 (Evans et al., 1992) (64%) and rat somatostatin receptors (Meyerhof et al., 1991 and Kluxen et al., 1992) (44%) (FIG. 1). MOR-1 also displays moderate homology (30–32%) with several G protein-coupled receptors, including the angiotensin II receptor, the interleukin-8 receptor, the N-formyl peptide receptor, and the C-C chemokine receptor. The sequence homology is lower ($\geq 25\%$) between MOR-1 and other G protein-coupled receptors, such as the adrenergic and muscarinic receptors (Collins et al., 1991). At the amino acid sequence level MOR-1 contains several sites that are conserved among other G protein-coupled receptors (Collins et al., 1991). Aspartic acid residues thought to interact with the protonated amine group of various ligands appear in putative transmembrane domains II and III, and two conserved cysteine residues believed to be involved in disulfide bonding occur in the first and second extracellular loop domains (Dixon et al., 1988). Both of these features are conserved between MOR-1 and the δ-opioid receptor (FIG. 1). In addition, MOR-1 displays a cysteine residue in the carboxyl-terminal region that is conserved among many G protein-coupled receptors which likely serves as a target for palmitoylation (Collins et al., 1991). There are also multiple sites in the second and third intracellular loops as well as the carboxyl-terminal region that can undergo phosphorylation via protein kinase A and protein kinase C Compared with the mouse δ-opioid receptor, MOR-1 contains five instead of two asparagine residues in the amino-terminal region that match the consensus sequence for N-linked glycosylation. These glycosylation sites are important in the modulation of receptor expression and function (Sumikawa K. and R. Miledi, 1989). The sequence of the MOR-1 cDNA has been submitted to GenBank (accession number L13069).

Example II
Expression of Rat Mu-Opioid Receptor

A 1.4-kilobase HindIII fragment encompassing the open reading frame from the cDNA encoding MOR-1 was cloned downstream of the human cytomegalovirus promoter in the mammalian expression vector pRc/CMV (Invitrogen). COS-7 cells grown in Dulbecco's modified Eagle's medium (Sigma D-5648) supplemented with 10% fetal bovine serum and 2 mM glutamine were transfected with supercoiled DNA by either electroporation or $CaPO_4$ co-precipitation (Graham, F. L. and A. J. Van Der Eb, 1973). Electroporation was performed in 0.4 cm cuvettes at 200 V, using $3\times10^6$ cells in a total volume of 0.5 ml containing growth medium, 40 μg of expression plasmid, and 200 μg of sheared salmon sperm DNA. Cells were harvested 48–72 hr after electroporation transfection.

The plasmid was transiently transfected into COS-7 cells to express MOR-1, and membranes from these cells were prepared. Cells were harvested by scraping into phosphate-buffered saline, pH 7.2, and centrifuged. Cell pellets were resuspended in lysis buffer (20 mM Tris-HCl, pH 7.4, 5 mM EDTA, 1 mM phenylmethylsulfonyl fluoride) and lysed with a Dounce homogenizer fitted with a tight pestle. The suspension was centrifuged for 10 min at 1000×g, and the supernatant was removed to a fresh tube. The pellet was resuspended in lysis buffer and centrifuged as described above. The supernatants were then combined and centrifuged for 20 min at 35,000×g. Membranes were washed in 50 mM Tris-HCl, PH 7.4, and centrifuged for 20 min at 35,000×g. The membrane pellets were then suspended in 50 mM Tris-HCl, pH 7.4. Protein concentrations were determined by the method of Bradford (Bradford, M. M., 1976).

Binding studies of membrane aliquots (15–50 μg/reaction) from the transfected COS-7 cells were carried out in 50 mM Tris-HCl, pH 7.4, 0.2% bovine serum albumin, at 4° for 90 min. A range of 0.01–2.5 nM [$^3$H] diprenorphine was used in the saturation assay and 0.25 nM was used for the displacement experiment The reactions were terminated by vacuum filtration through Whatman GF/B filters which were pretreated with 1% polyethylenimine. Nonspecific binding was determined using 5 μM naloxone.

Figure 2:
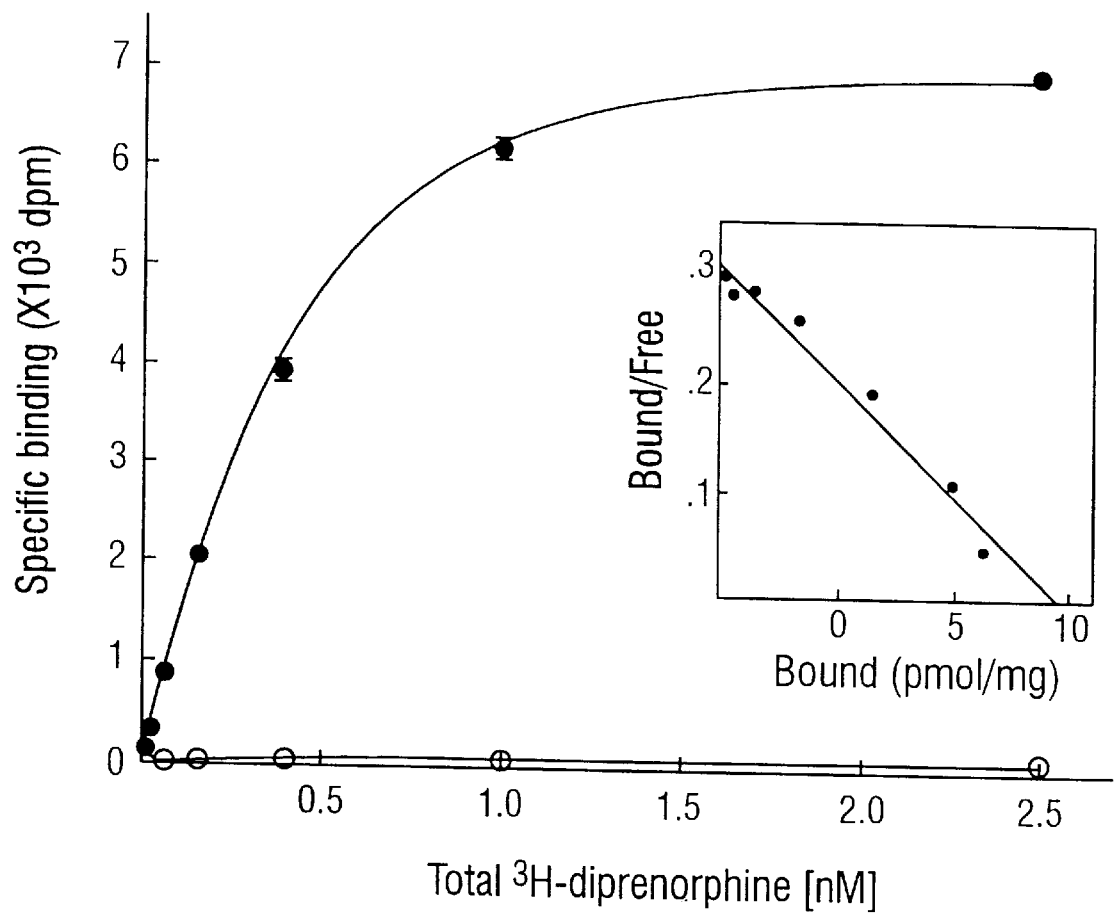

Saturation binding of membranes was performed using [$^3$H]diprenorphine (Magnan et al., 1982), a nonselective opioid antagonist with high affinity for all three types of opioid receptors FIG. 2. Membranes of COS cells transfected with the MOR-1 plasmid displayed [$^3$H] diprenorphine binding with a dissociation constant ($K_d$) value of 0.3±0.09 nM (mean±standard error, five experiments). This is one tenth the $K_d$ value (3.8 nm) reported for the cloned mouse δ-opioid receptor (Evans et al., 1992).

Various ligands which displace [$^3$H]diprenorphine binding were used to characterize the pharmacological features of MOR-1. The inhibition constant $K_i$ values were obtained from three binding experiments for each ligand and are listed in Table 2.

TABLE 2

| Ligand | $K_i$ values (nM) |
| --- | --- |
| Agonists | |
| (DAGO) (DAMGO) | 2.8 ± 0.2 |
| (DADLE) | 55 ± 17 |
| (DSLET) | 314 ± 35 |
| U-50488 | 1,551 ± 307 |
| (DPDPE) | 7,297 ± 1,092 |
| Antagonists and Somatostatins | |
| Naloxone | 1.0 ± 0.6 |
| β-funaltrexamine (β-FNA) | 1.3 ± 0.1 |
| Naloxonazine | 2.4 ± 0.9 |
| Cyprodime | 9.1 ± 2.8 |
| Cyclic somatostatin | 10,994 ± 6,777 (IC$_{50}$) |
| Somatostatin-1-14 | 730,000 (IC$_{50}$) |

The μ-selective agonist [D-Ala$^2$, N—Me'Phe$^4$, Gly—ol$^5$]-enkephalin (DAGO) displaced diprenorphine binding with high affinity ($K_i$=2.8 nM), whereas the δ-selective agonist [D-Pen$^{25}$]-enkephalin (DPDPE) and the κ-selective agonist U-50488 showed low affinities, with $K_i$ values in the micromolar range (Pasternak et al.,, 1980). [D-Ala$^2$, D-Leu$^5$]-enkephalin (DADLE) and [D-Ser$^2$, Leu$^5$, Thr$^6$]-enkephalin (DSLET), two predominantly δ agonists that have previously been shown to interact with μ receptors (Barrett, R. W. and J. L Vaught, 1983; Itzhak, Y. and G. W. Pasternak, 1987), showed binding to MOR-1 with moderate affinities ($K_i$=55 and 314 nM, respectively). The rank order of potency for these opioid agonists is DAGO>DADLE>DSLET>U-50488>DPDPE which is the pharmacological profile of μ receptors. Displacement of diprenorphine binding to MOR-1 was performed with three μ-selective antagonists, β-FNA, naloxonazine, and cyprodime (Ward et al., 1985; Nishimura et al., 1984; Curciani et al., 1987; Schmidhammer et al., 1990). All three ligands exhibited high potency in displacing diprenorphine binding to MOR-1 with $K_i$ values in the nanomolar range (Table 1). The order of potency for opioid agonists and the nanomolar affinity for μ-selective antagonists indicates that MOR-1 is a μ-opioid receptor.

The sequence homology between rat μ-opioid receptor encoded by MOR-1 cDNA and the somatostatin receptors is noteworthy. Many somatostatin analogues, especially those of the cyclic form, have been shown to interact with μ-opioid receptors, and some of them have been used as μ-selective antagonists (Gulya et al., 1986). Displacement binding experiments were performed using two somatostatin ligands, somatostatin-1-14 and cyclic somatostatin. Somatostatin-1-14 did not displace [$^3$H]diprenorphine binding to the rat μ receptor encoded by the MOR-1 cDNA, at concentrations as high as 30 μM, whereas cyclic somatostatin competed with diprenorphine binding with an IC$_{50}$ value in the micromolar range FIG. 3A and FIG. 3B; Table 1).

All three classes of opioid receptors are coupled to adenylyl cyclase (Childers S. R, 1993; Cox, B. M., 1993; Sharma et al., 1975). cAMP levels were determined in COS-7 cells after exposure to μ-selective ligands to examine whether the μ receptor is coupled to intracellular signaling pathways. COS-7 cells transiently expressing the MOR-1 plasmid cDNA were harvested 48 hrs after transfection and were resuspended in growth medium. Cells were treated with 10 μM forskolin in the presence of 1 mM 3-isobutyl-1-methylxanthine at 37° for 10 min. DAGO (100 nM) and naloxonazine (10 μM) were included during forskolin treatment where indicated. Cells were pelleted and then solubilized in 0.1 N HCl. After extraction with water-saturated ether, the supernatants were lyophilized. cAMP was assayed using a commercially available radioimmunoassay kit (DuPont/NEN). Results are shown in FIG. 14. In nontransfected COS-7 cells, treatment with these ligands did not cause significant changes in the intracellular cAMP levels. In transfected cells expressing the μ receptor, the μ-specific agonist DAGO reduced cAMP levels significantly (18.1±25% reduction from control, p<0.05). This inhibitory effect on adenylyl cyclase activity by DAGO was blocked by the μ-selective antagonist naloxonazine. It has been reported that μ-opioid receptors exert an inhibitory effect on adenylyl cyclase activity (Frey, E. A. and J. W. Kebabian, 1984) and that activation of μ receptors in a human neuroblastoma cell line reduces intracellular cAMP levels by approximately 20% (Yu et al., 1986). Our data are consistent with these reports and shows that the μ-opioid receptor encoded by MOR-1 is functionally coupled to the inhibition of adenylyl cyclase.

Example III
Stable Transfection of Mammalian Cells

Stably transfected cultured mammalian cells were generated by transfecting chinese hamster ovary cells (CHO) with the vector pRc/CMV which contained a cDNA coding for a mu opioid receptor. CHO cells from the American Type Culture Collection were plated at a density of 5×10$^4$ cells/

100 mm plate one day before transfection. The CHO cells were incubated at 37° C. in a humidified chamber with 5% $CO_2$, in DME (Sigma), supplemented with 2 mM glutamine and 10% fetal bovine serum. The culture medium was changed 4–6 hours before transfection. The plasmid DNA was transfected into cells using the calcium phosphate precipitation method (Graham and Van Der Eb, 1973). After the $CaPO_4$ precipitation, the plates were incubated in a 3% $CO_2$, humidified chamber at 37° C. After 15–24 hr at 3% $CO_2$, the cells were washed with Hank's balanced salt solution, fresh culture medium was added, and the cells were transferred to a 5% $CO_2$, humidified incubator at 37° C. After 24 hr at 5% $CO_2$, selection for neomycin resistance was initiated by replacing the culture medium with medium containing 500 μg/ml of G418 (Sigma). G418 is a neomycin analogue that is permeable to mammalian cell membranes. The selection medium was changed every 2–3 days until drug-resistant colonies formed (2–3 weeks). Individual colonies were picked and replated after trypsin dissociation. A second round of selection was performed to isolate clonal derivatives. G418 resistant colonies were then allowed to grow in G418 medium until the plates were confluent. Aliquots of cells G418 resistant cells were frozen in liquid nitrogen for long-term storage of the transfected cells.

The expression of the mu opioid receptor in stably transfected CHO cells was demonstrated by saturation binding studies using a range of 0.2–20 mM $^3$H-DAGO. Membranes from G418 resistant CHO cells were prepared as described in Example II above. The $B_{MAX}$ of $^3$H-DAGO binding to membranes from stably transfected CHO cells was 660 nmole/mg protein, and the $K_D$ is ~1 nM for $^3$H-DAGO. These values are comparable to the values obtained for $^3$H-DAGO binding to mu opioid receptors obtained from transient transfections of COS-7 cells.

As expected for stable transfectants, different clonal derivatives gave different levels of receptor expression. For example, clones #15 and #18 had 1 and 3 picomoles of the receptor per milligrams of membrane protein, respectively as determined by ligand binding.

Functional characteristics of the expressed mu opioid receptor in stable transfection were also determined by assaying the GTPase activity of G proteins (Koshi and Klee, 1981). Upon stimulation by 10 μM DAMGO, the GTPase activity was increased by 30%, indicating that the G proteins were activated by the mu opioid receptor. This effect of DAMGO was blocked by naloxone.

REFERENCES CITED

The references listed below as well as all references cited in the specification are incorporated herein by reference to the extent that they supplement, explain, provide a background for or teach methodology, techniques and/or compositions employed herein.

Adelman et al. (1983) *DNA* 2:183.
Akil, H. et al. (1984) *Annu. Rev. Neurosci.* 7:223.
Attali, B. et al. (1989) *J. Neurochem.* 52:360.
Barrett, R. W. and J. L. Vaught (1983) *Life Sci.* 33:2439.
Berg J. M. (1988) *Proc. Natl. Acad. Sci. U.S.A.* 85:99–102.
Bertin, B. et al. (1992) *J. Biol. Chem.* 267(12):8200.
Bero et al. (1988) *Mol. Pharmacol.* 34:614.
Bertolucci, M. et al. *Neurosci. Abstr.* 18L1368.
Bolivar et al. (1977) *Gene*, 2:95.
Boshart et al. (1985) *Cell* 41:521.
Bouvier, M. et al. (1988) *Mol. Pharmacol.* 33:133.
Bradford, M. M. (1976) *Anal. Biochem.* 72:248.
Bradbury, A. F. et al. (1976) *Nature* 260:165.
Breder, C. D. et al. (1992). *J. Neurosci* 12:3920.
Butt et al. (1990) *Biophys. J.* 58:1473.
Chang et al. (1978) *Nature*, 375:615.
Childers, S. R. (1993) *Handb. Exp. Pharmacol. Sci.* 104:189.
Clark, J. A. et al. (1989) *J. Pharmacol. Expt. Therapeut.* 251:461.
Collins et al. (1991) *Vitam. Horm.* 46:1.
Corbett et al. (1993) *Handb. Exp. Pharmacol. Sci* 8:456.
Cotecchia et al. (1988) *Proc. Natl. Acad. Sci. USA* 85:7159.
Cotecchia et al. (1990) *Proc. Natl. Acad. Sci. USA* 87:2896.
Cox, B. M. (1993) *Handb. Exp. Pharmacol. Sci.* 104:145.
Crea et al. (1978) *Proc. Natl. Acad. Sci. U.S.A.*, 75:5765.
Cruciani et al. (1987) J. Pharmacol. Exp. Ther. 24215.
Danboldt, N. C. et al. (1990) *Biochemistry* 29(28):6734.
DiChiara, G. et al. (1992) *Trends Pharmacol. Sci.* 13:185.
Dohlman (1987) *Biochemistry* 26:2657.
Dohlman, H. G. (1991) Annu. Rev. Biochem. 60:166–170; 174–s176; 653–688.
Drake et al. (1989) *Science* 243:1586.
Durbin, S. D. and W. E. Carlson (1992) *J. Crystal Growth* 122:71.
Edstrom et al. (1990) *Biophys. J.* 58:1437.
Evans et al. (1992) *Science* 258:1952.
Evans, R. M. and S. M. Hollenberg (1988) *Cell* 52:1–3.
Dixon et al. (1988) *Cold Spring Harbor Symp. Quant. Biol.* 53:487.
Ferruti, P. and M. C. Tanzi, (1986) *Cris. Rev. Ther. Drug Carrier Syst.* 2:117.
Fiers et al. (1978) *Nature* 273:113.
Frey, E. A and J. W. Kebabian (1984) *Endocrinology* 115:1797.
Frielle, T. et al. (1988) *Proc. Natl. Acad. Sci. USA* 85:9484.
Gabizon, A. et al. (1990) *Cancer Res.* 50:6371–6378.
Gioannini, T. L. et al. (1989) *J. Mol. Recogn.* 2:44.
Goeddel et al. (1979) *Nature*, 281:544.
Goeddel et al. (1980) *Nucleic Acids Res.*, 8:4057.
Graham, F. L and A. J. Van Der Eb (1973) *Virology* 52:456.
Gransch, C. et al. (1988) *J. Biol. Chem.* 263:5853.
Gulya et al. (1986) *Life Sci.* 38:2221.
Hansma et al. (1992) *Science* 256:1180.
Harlow, E. and D. Lane (1988) *Antibodies: "A Laboratory Manual,"* Cold Spring Harbor Laboratory.
Henderson et al. (1992) *Science* 257:1944.
Hess et al. (1968) *J. Adv. Enzyme Reg.* 7:149.
Hitzeman et al. (1980) *J. Biol. Chem.* 255:2073.
Hob et al (1991) *Science* 253:1405.
Holland et al. (1978) *Biochemistry* 17:4900.
Horstman, D. A et al. (1990) *J. Biol. Chem.* 265:21590.
Hsia, J. A et al. (1984) *J. Biol. Chem.* 259:1086.
Hughes, J. et al. (1975) *Nature* 258:577.
Itakura et al. (1977) *Science* 198:1056.
Itzbak, Y. and G. W. Pasternak (1987) *Life Sci.* 40:307.
Johnson et al. (1990) *Mol. Pharm.*, 38:289.
Jones (1977) *Genetics* 85:12.
Kanaho et al. (1984) *J. Biol. Chem.* 259:7378.
Kennelly, P. J. et al. (1991) *J. Biol. Chem.* 266:15555.
Kieffer et al. (1992) *Proc. Natl. Acad. Sci. USA* 89:12048.
King et al. (1990) *Science* 250:121.
Kingsman et al. (1979) *Gene* 7:141.
Klug, A. and D. Rhodes (1987) *Trends Biochem. Sci.* 12:464–469.
Kluxen et al. (1992) *Proc. Natl. Acad. Sci. USA* 89:4618.
Kobilka, B. K. et al. (1987) *J. Biol. Chem.* 262:7321.
Kobilka, B. K. et al. (1988) *Science* 240:1310.
Koob, G. F. et al. (1992) *Trends Neurosci.* 15:186.
Koshi, G. and W. A. Klee (1981) *Proc. Natl. Acad. Sci. USA* 78:4185.

Kozasa et al. (1988) *Proc. Natl. Acad. Sci USA* 85:2081.
Kruse and Patterson, eds. (1973) *Tissue Culture*, Academic Press.
Kyte, J., and R. F. Doolittle (1982) *J. Mol. Biol.* 157:105.
Lal et al. (1993) *Am. J. Physiol. in press*.
Lal, R. and L. Yu (1993) *Proc. Natl. Acad. Sci. USA*, 90:7280.
Loh, H. H. et al. (1990) *Annu. Rev. Pharmacol. Toxicol.* 30:123.
Lomasney et al. (1990) *Proc. Natl. Acad. Sci. USA* 87:5094.
Lutz, R. A et al. (1992) *J. Receptor Res.* 12:267.
Magnan et al. (1982) *Naunyn-Schmiedebergs Arch. Pharmacol.* 319:197.
Mansour, A. et al. (1987) *J. Neurosci.* 7:2445.
Marullo et al. (1988) *Proc. Natl. Acad. Sci. USA* 85:7551.
Messing et al., *Third Cleveland Symposium on Macromolecules and Recombinant DNA*, Editor A. Walton, Elsevier, Amsterdam (1981).
Meryerhof et al. (1991) *DNA Cell Biol.* 10:689.
Miller, J. et al. (1985) *EMBO J.* 4:1609–1614.
Nathans et al. (1986 A) *Science* 232:193.
Nathans et al. (1986 B) *Science* 232:203.
Nishimura et al. (1984) *Mol. Pharmacol.* 25:29.
Nock, B. et al. (1988) *Eur. J. Pharmacol.* 154:27.
Okayama et al. (1983) *Mol. Cell Biol.* 3:280.
Olson, G. A. et al. (1989) *Peptides* 10:1253.
Ott, S. et al. (1988) *J. Biol. Chem.* 263:10524.
Parker, E. and E. M. Ross (1991) *J. of Biol. Chem.* 266:15.
Pasternak, G. W. (1988) *The Opiate Receptors* Humana Press, Clifton, N.J.
Payette et al. (1990) *FEBS Lett.* 266–21.
Payre, F. and A Vincent (1988) *FEBS Lett.* 234:245–250.
Pert, C. G. et al. (1973) *Science* 179:1011.
Pert, C. B. et al. (1974) *Mol. Pharmacol.* 10:868.
Pfeiffer, A. et al. (1986) *Science* 223:774.
Puttfarcken, P. S. et al. (1988) *Mol. Pharmacol.* 33:520.
Ranade, V. V. (1989) *J. Clin. Pharmacol.* 29:685–694
Regan et al. (1988) *Proc. Natl. Acad. Sci. USA* 85:6301.
Sambrook, J. et al. (1989) *Molecular Cloning: A Laboratory Manual* (Cold Spring Harbor Laboratory Press, Cold Spring Harbor, N.Y.).
Schmidhammer et al. (1990) *Prog. Clin. Biol. Res.* 328:37.
Seeburg (1982) *DNA* 1:239.
Sharma et al. (1975) *Proc. Natl. Acad. Sci. USA* 72:590.
Shook, J. E. et al. (1990) *Am. Rev. Respir. Dis.* 142:895.
Siebwenlist et al. (1980) *Cell,* 20:269.
Simon, E. J. (1991) *Medicinal Res. Rev.* 11:357.
Snutch et al. (1990) *Proc. Natl. Acad. Sci. USA* 87:3391.
Stinchcomb et al. (1979) *Nature,* 282:39.
Stratford-Perricaudet et al. (1992).
Strotchman and Simon (1991).
Sumikawa, K and R. Miledi (1989) *Mol. Brain Res.* 5:183.
Thomsen et al. (1984) *PNAS* 81:659.
Tschemper et al. (1980) *Gene* 10:157.
Unterwald, E. M. et al. (1991) *Brain Res.* 562:57.
Unterwald, E. M. et al. (1987) *Eur. J. Pharmacol.* 133:275.
Ward et al. (1985) *Eur. J. Pharmacol.* 107:323.
Weisenhorn et al. (1990) *Biophys J.* 58:1251.
Xie, G-X. et al. (1992) *Proc. Natl. Acad. Sci. USA* 89:4124.
Yamada, Y. et al. (1992) *Proc. Natl. Acad. Sci. USA* 89:251.
Yasuda, K et al. (1992) *J. Biol. Chem.* 267:20422.
Yokota, Y. et al. (1992) *EMBO J.* 11:3585.
Yu et al. (1986) *J. Biol. Chem.* 261:1065.
Zukin, R. S. et al. (1988) *Proc. Natl. Acad. Sci. USA* 85:4061.

---

What is claimed is:

1. An isolated and purified polynucleotide that encodes a mammalian mu opioid receptor polypeptide, said polypeptide comprising an amino acid residue sequence of SEQ ID NO:2.

2. The isolated and purified polynucleotide of claim 1, wherein said polynucleotide is a DNA molecule.

3. The isolated and purified polynucleotide of claim 1, wherein said polynucleotide comprises the nucleotide base sequence of SEQ ID NO:1.

4. An isolated and purified polynucleotide comprising a base sequence that is identical or complementary to a segment of at least 35 contiguous bases of SEQ ID NO:1.

5. An expression vector comprising a polynucleotide that encodes a mammalian mu opioid receptor polypeptide, wherein said polynucleotide has a sequence having at least 35 contiguous bases identical to SEQ ID NO:1 or its complement and said polynucleotide is capable of hybridizing to SEQ ID NO:1 or its complement under a hybridization condition involving 0.02M–0.15M NaCl at a temperature of about 50° C. to about 70° C.

6. A recombinant host cell transfected with a polynucleotide that encodes a mammalian mu opioid receptor polypeptide, wherein said polynucleotide has a sequence having at least 35 contiguous bases identical to SEQ ID NO:1 or its complement and said polynucleotide is capable of hybridizing to SEQ ID NO:1 or its complement under a hybridization condition involving 0.02M–0.15M NaCl at a temperature of about 50° C. to about 70° C.

7. A process of preparing a mammalian mu opioid receptor polypeptide comprising (a) transfecting a cell with a polynucleotide that encodes a mammalian mu opioid receptor polypeptide, wherein said polynucleotide has a sequence having at least 35 contiguous bases identical to SEQ ID NO:1 or its complement and said polynucleotide is capable of hybridizing to SEQ ID NO:1 or its complement under a hybridization condition involving 0.02M–0.15M NaCl at a temperature of about 50° C. to about 70° C.;

(b) maintaining the transformed host cell under biological conditions sufficient for expression of the polypeptide; and (c) recovering the receptor.

8. The isolated and purified polynucleotide of claim 4, further defined as comprising the base sequence of SEQ ID NO:1.

9. The isolated and purified polynucleotide of claim 4, further defined as encoding a full length mammalian mu opioid receptor wherein said polynucleotide is capable of hybridizing to SEQ ID NO:1 or its complement under a hybridization condition involving 0.02M–0.15M NaCl at a temperature of about 50° C. to about 70° C.

10. The isolated and purified polynucleotide of claim 4, further defined as encoding a human mu opioid receptor wherein said polynucleotide is capable of hybridizing to SEQ ID NO:1 or its complement under a hybridization condition involving 0.02M–0.15M NaCl at a temperature of about 50° C. to about 70° C.

11. The isolated and purified polynucleotide of claim 4, further defined as comprising a base sequence that is identical or complementary to a segment of at least 55 contiguous bases of SEQ ID NO:1.

12. The expression vector of claim 5, wherein said polynucleotide has a sequence in which at least 55 contiguous bases identical to or complementary to at least 55 contiguous bases of SEQ ID NO:1.

13. The recombinant host cell of claim 6, wherein the polynucleotide that encodes a mammalian mu opioid receptor polypeptide has at least 55 contiguous bases that are identical to or complementary to 55 contiguous bases of SEQ ID NO:1.

14. The process of claim 7, wherein the polynucleotide that encodes a mammalian mu opioid receptor polypeptide has a sequence in which at least 55 contiguous bases are identical to or complementary to 55 contiguous bases of SEQ ID NO:1.

15. An expression vector comprising a polynucleotide comprising a base sequence that is identical or complementary to a segment of at least 35 contiguous bases of SEQ ID NO:1.

* * * * *

UNITED STATES PATENT AND TRADEMARK OFFICE
CERTIFICATE OF CORRECTION

PATENT NO.    : 6,235,496 B1
DATED         : May 22, 2001
INVENTOR(S)   : Lei Yu

It is certified that error appears in the above-identified patent and that said Letters Patent is hereby corrected as shown below:

<u>Title page,</u>
Item [54], please delete "NUCLEIC ACID ENCODING MAMMALIAN MUOPIOID RECEPTOR" and insert -- MU OPIOID RECEPTOR:COMPOSITIONS AND METHODS -- therefor.

Signed and Sealed this

Twenty-ninth Day of January, 2002

Attest:

*Attesting Officer*

JAMES E. ROGAN
*Director of the United States Patent and Trademark Office*

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 1618 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 214..1407

(xi) SEQUENCE DESCRIPTION: SEQ ID NO:1:

```
CGTGGAAGGG GGCTACAAGC AGAGGAGAAT ATCAGACGCT CAGACGTTCC CTTCTGCCTG      60

CCGCTCTTCT CTGGTTCCAC TAGGGCTGGT CCATGTAAGA ATCTGACGGA GCCTAGGGCA     120

GCTGTGAGAG GAAGAGGCTG GGGCGCGTGG AACCCGAAAA GTCTGAGTGC TCTCAGTTAC     180

AGCCTACCTA GTCCGCAGCA GGCCTTCAGC ACC ATG GAC AGC AGC ACC GGC CCA     234
                                    Met Asp Ser Ser Thr Gly Pro
                                     1               5

GGG AAC ACC AGC GAC TGC TCA GAC CCC TTA GCT CAG GCA AGT TGC TCC      282
Gly Asn Thr Ser Asp Cys Ser Asp Pro Leu Ala Gln Ala Ser Cys Ser
         10                  15                  20

CCA GCA CCT GGC TCC TGG CTC AAC TTG TCC CAC GTT GAT GGC AAC CAG      330
```

-continued

```
Pro Ala Pro Gly Ser Trp Leu Asn Leu Ser His Val Asp Gly Asn Gln
         25                  30                  35

TCC GAT CCA TGC GGT CTG AAC CGC ACC GGG CTT GGC GGG AAC GAC AGC      378
Ser Asp Pro Cys Gly Leu Asn Arg Thr Gly Leu Gly Gly Asn Asp Ser
 40                  45                  50                  55

CTG TGC CCT CAG ACC GGC AGC CCT TCC ATG GTC ACA GCC ATT ACC ATC      426
Leu Cys Pro Gln Thr Gly Ser Pro Ser Met Val Thr Ala Ile Thr Ile
                 60                  65                  70

ATG GCC CTC TAC TCT ATC GTG TGT GTA GTG GGC CTC TTC GGA AAC TTC      474
Met Ala Leu Tyr Ser Ile Val Cys Val Val Gly Leu Phe Gly Asn Phe
             75                  80                  85

CTG GTC ATG TAT GTG ATT GTA AGA TAC ACC AAA ATG AAG ACT GCC ACC      522
Leu Val Met Tyr Val Ile Val Arg Tyr Thr Lys Met Lys Thr Ala Thr
         90                  95                 100

AAC ATC TAC ATT TTC AAC CTT GCT CTG GCA GAC GCC TTA GCG ACC AGT      570
Asn Ile Tyr Ile Phe Asn Leu Ala Leu Ala Asp Ala Leu Ala Thr Ser
105                 110                 115

ACA CTG CCC TTT CAG AGT GTC AAC TAC CTG ATG GGA ACA TGG CCC TTC      618
Thr Leu Pro Phe Gln Ser Val Asn Tyr Leu Met Gly Thr Trp Pro Phe
120                 125                 130                 135

GGA ACC ATC CTC TGC AAG ATC GTG ATC TCA ATA GAT TAC TAC AAC ATG      666
Gly Thr Ile Leu Cys Lys Ile Val Ile Ser Ile Asp Tyr Tyr Asn Met
                140                 145                 150

TTC ACC AGC ATA TTC ACC CTC TGC ACC ATG AGC GTG GAC CGC TAC ATT      714
Phe Thr Ser Ile Phe Thr Leu Cys Thr Met Ser Val Asp Arg Tyr Ile
            155                 160                 165

GCT GTC TGC CAC CCA GTC AAA GCC CTG GAT TTC CGT ACC CCC CGA AAT      762
Ala Val Cys His Pro Val Lys Ala Leu Asp Phe Arg Thr Pro Arg Asn
        170                 175                 180

GCC AAA ATC GTC AAC GTC TGC AAC TGG ATC CTC TCT TCT GCC ATC GGT      810
Ala Lys Ile Val Asn Val Cys Asn Trp Ile Leu Ser Ser Ala Ile Gly
185                 190                 195

CTG CCT GTA ATG TTC ATG GCA ACC ACA AAA TAC AGG CAG GGG TCC ATA      858
Leu Pro Val Met Phe Met Ala Thr Thr Lys Tyr Arg Gln Gly Ser Ile
200                 205                 210                 215

GAT TGC ACC CTC ACG TTC TCC CAC CCA ACC TGG TAC TGG GAG AAC CTG      906
Asp Cys Thr Leu Thr Phe Ser His Pro Thr Trp Tyr Trp Glu Asn Leu
                220                 225                 230

CTC AAA ATC TGT GTC TTT ATC TTC GCT TTC ATC ATG CCG ATC CTC ATC      954
Leu Lys Ile Cys Val Phe Ile Phe Ala Phe Ile Met Pro Ile Leu Ile
            235                 240                 245

ATC ACT GTG TGT TAC GGC CTG ATG ATC TTA CGA CTC AAG AGC GTT CGC     1002
Ile Thr Val Cys Tyr Gly Leu Met Ile Leu Arg Leu Lys Ser Val Arg
        250                 255                 260

ATG CTA TCG GGC TCC AAA GAA AAG GAC AGG AAT CTG CGC AGG ATC ACC     1050
Met Leu Ser Gly Ser Lys Glu Lys Asp Arg Asn Leu Arg Arg Ile Thr
265                 270                 275

CGG ATG GTG CTG GTG GTC GTG GCT GTA TTT ATC GTC TGC TGG ACC CCC     1098
Arg Met Val Leu Val Val Val Ala Val Phe Ile Val Cys Trp Thr Pro
280                 285                 290                 295

ATC CAC ATC TAC GTC ATC ATC AAA GCG CTG ATC ACG ATT CCA GAA ACC     1146
Ile His Ile Tyr Val Ile Ile Lys Ala Leu Ile Thr Ile Pro Glu Thr
                300                 305                 310

ACA TTT CAG ACC GTT TCC TGG CAC TTC TGC ATT GCT TTG GGT TAC ACG     1194
Thr Phe Gln Thr Val Ser Trp His Phe Cys Ile Ala Leu Gly Tyr Thr
            315                 320                 325

AAC AGC TGC CTG AAT CCA GTT CTT TAC GCC TTC CTG GAT GAA AAC TTC     1242
Asn Ser Cys Leu Asn Pro Val Leu Tyr Ala Phe Leu Asp Glu Asn Phe
        330                 335                 340
```

```
AAG CGA TGC TTC AGA GAG TTC TGC ATC CCA ACC TCG TCC ACG ATC GAA      1290
Lys Arg Cys Phe Arg Glu Phe Cys Ile Pro Thr Ser Ser Thr Ile Glu
    345                 350                 355

CAG CAA AAC TCC ACT CGA GTC CGT CAG AAC ACT AGG GAA CAT CCC TCC      1338
Gln Gln Asn Ser Thr Arg Val Arg Gln Asn Thr Arg Glu His Pro Ser
360                 365                 370                 375

ACG GCT AAT ACA GTG GAT CGA ACT AAC CAC CAG CTA GAA AAT CTG GAG      1386
Thr Ala Asn Thr Val Asp Arg Thr Asn His Gln Leu Glu Asn Leu Glu
                380                 385                 390

GCA GAA ACT GCT CCA TTG CCC TAACTGGGTC TCACACCATC CAGACCCTCG         1437
Ala Glu Thr Ala Pro Leu Pro
                395

CTAAGCTTAG AGGCCGCCAT CTACGTGGAA TCAGGTTGCT GTCAGGGTGT GTGGGAGGCT    1497

CTGGTTTCCT GAGAAACCAT CTGATCCTGC ATTCAAAGTC ATTCCTCTCT GGCTACTTCA    1557

CTCTGCACAT GAGAGATGCT CAGACTGATC AAGACCAGAA GAAAGAAGAG ACTACCGGAC    1617

A                                                                   1618

(2) INFORMATION FOR SEQ ID NO:2:

(i) SEQUENCE CHARACTERISTICS:
        (A) LENGTH: 398 amino acids
        (B) TYPE: amino acid
        (D) TOPOLOGY: linear (ii) MOLECULE TYPE: protein (xi) SEQUENCE DESCRIPTION: SEQ ID NO:2:

Met Asp Ser Ser Thr Gly Pro Gly Asn Thr Ser Asp Cys Ser Asp Pro
1               5                   10                  15

Leu Ala Gln Ala Ser Cys Ser Pro Ala Pro Gly Ser Trp Leu Asn Leu
                20                  25                  30

Ser His Val Asp Gly Asn Gln Ser Asp Pro Cys Gly Leu Asn Arg Thr
            35                  40                  45

Gly Leu Gly Gly Asn Asp Ser Leu Cys Pro Gln Thr Gly Ser Pro Ser
        50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
                100                 105                 110

Ala Asp Ala Leu Ala Thr Ser Thr Leu Pro Phe Gln Ser Val Asn Tyr
            115                 120                 125

Leu Met Gly Thr Trp Pro Phe Gly Thr Ile Leu Cys Lys Ile Val Ile
        130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
        195                 200                 205

Lys Tyr Arg Gln Gly Ser Ile Asp Cys Thr Leu Thr Phe Ser His Pro
    210                 215                 220

Thr Trp Tyr Trp Glu Asn Leu Leu Lys Ile Cys Val Phe Ile Phe Ala
```

```
225                 230                 235                 240
Phe Ile Met Pro Ile Leu Ile Ile Thr Val Cys Tyr Gly Leu Met Ile
                245                 250                 255
Leu Arg Leu Lys Ser Val Arg Met Leu Ser Gly Ser Lys Glu Lys Asp
                260                 265                 270
Arg Asn Leu Arg Arg Ile Thr Arg Met Val Leu Val Val Val Ala Val
                275                 280                 285
Phe Ile Val Cys Trp Thr Pro Ile His Ile Tyr Val Ile Ile Lys Ala
                290                 295                 300
Leu Ile Thr Ile Pro Glu Thr Thr Phe Gln Thr Val Ser Trp His Phe
305                 310                 315                 320
Cys Ile Ala Leu Gly Tyr Thr Asn Ser Cys Leu Asn Pro Val Leu Tyr
                325                 330                 335
Ala Phe Leu Asp Glu Asn Phe Lys Arg Cys Phe Arg Glu Phe Cys Ile
                340                 345                 350
Pro Thr Ser Ser Thr Ile Glu Gln Gln Asn Ser Thr Arg Val Arg Gln
                355                 360                 365
Asn Thr Arg Glu His Pro Ser Thr Ala Asn Thr Val Asp Arg Thr Asn
                370                 375                 380
His Gln Leu Glu Asn Leu Glu Ala Glu Thr Ala Pro Leu Pro
385                 390                 395
```

(2) INFORMATION FOR SEQ ID NO:3:

(i) SEQUENCE CHARACTERISTICS:
        (A) LENGTH: 1618 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 339..1232

(xi) SEQUENCE DESCRIPTION: SEQ ID NO:3:

```
CGTGGAAGGG GGCTACAAGC AGAGGAGAAT ATCAGACGCT CAGACGTTCC CTTCTGCCTG      60

CCGCTCTTCT CTGGTTCCAC TAGGGCTGGT CCATGTAAGA ATCTGACGGA GCCTAGGGCA     120

GCTGTGAGAG GAAGAGGCTG GGGCGCGTGG AACCCGAAAA GTCTGAGTGC TCTCAGTTAC     180

AGCCTACCTA GTCCGCAGCA GGCCTTCAGC ACCATGGACA GCAGCACCGG CCCAGGGAAC     240

ACCAGCGACT GCTCAGACCC CTTAGCTCAG GCAAGTTGCT CCCCAGCACC TGGCTCCTGG     300

CTCAACTTGT CCCACGTTGA TGGCAACCAG TCCGATCC ATG CGG TCT GAA CCG         353
                                           Met Arg Ser Glu Pro
                                             1               5

CAC CGG GCT TGG CGG GAA CGA CAG CCT GTG CCC TCA GAC CGG CAG CCC       401
His Arg Ala Trp Arg Glu Arg Gln Pro Val Pro Ser Asp Arg Gln Pro
             10                  15                  20

TTC CAT GGT CAC AGC CAT TAC CAT CAT GGC CCT CTA CTC TAT CGT GTG       449
Phe His Gly His Ser His Tyr His His Gly Pro Leu Leu Tyr Arg Val
         25                  30                  35

TGT AGT GGG CCT CTT CGG AAA CTT CCT GGT CAT GTA TGT GAT TGT AAG       497
Cys Ser Gly Pro Leu Arg Lys Leu Pro Gly His Val Cys Asp Cys Lys
     40                  45                  50

ATA CAC CAA AAT GAA GAC TGC CAC CAA CAT CTA CAT TTT CAA CCT TGC       545
Ile His Gln Asn Glu Asp Cys His Gln His Leu His Phe Gln Pro Cys
 55                  60                  65

TCT GGC AGA CGC CTT AGC GAC CAG TAC ACT GCC CTT TCA GAG TGT CAA       593
Ser Gly Arg Arg Leu Ser Asp Gln Tyr Thr Ala Leu Ser Glu Cys Gln
```

```
         70                 75                  80                  85
CTA CCT GAT GGG AAC ATG GCC CTT CGG AAC CAT CCT CTG CAA GAT CGT              641
Leu Pro Asp Gly Asn Met Ala Leu Arg Asn His Pro Leu Gln Asp Arg
             90                  95                 100

GAT CTC AAT AGA TTA CTA CAA CAT GTT CAC CAG CAT ATT CAC CCT CTG              689
Asp Leu Asn Arg Leu Leu Gln His Val His Gln His Ile His Pro Leu
            105                 110                 115

CAC CAT GAG CGT GGA CCG CTA CAT TGC TGT CTG CCA CCC AGT CAA AGC              737
His His Glu Arg Gly Pro Leu His Cys Cys Leu Pro Pro Ser Gln Ser
            120                 125                 130

CCT GGA TTT CCG TAC CCC CCG AAA TGC CAA AAT CGT CAA CGT CTG CAA              785
Pro Gly Phe Pro Tyr Pro Pro Lys Cys Gln Asn Arg Gln Arg Leu Gln
        135                 140                 145

CTG GAT CCT CTC TTC TGC CAT CGG TCT GCC TGT AAT GTT CAT GGC AAC              833
Leu Asp Pro Leu Phe Cys His Arg Ser Ala Cys Asn Val His Gly Asn
150                 155                 160                 165

CAC AAA ATA CAG GCA GGG GTC CAT AGA TTG CAC CCT CAC GTT CTC CCA              881
His Lys Ile Gln Ala Gly Val His Arg Leu His Pro His Val Leu Pro
                170                 175                 180

CCC AAC CTG GTA CTG GGA GAA CCT GCT CAA AAT CTG TGT CTT TAT CTT              929
Pro Asn Leu Val Leu Gly Glu Pro Ala Gln Asn Leu Cys Leu Tyr Leu
            185                 190                 195

CGC TTT CAT CAT GCC GAT CCT CAT CAT CAC TGT GTG TTA CGG CCT GAT              977
Arg Phe His His Ala Asp Pro His His His Cys Val Leu Arg Pro Asp
            200                 205                 210

GAT CTT ACG ACT CAA GAG CGT TCG CAT GCT ATC GGG CTC CAA AGA AAA             1025
Asp Leu Thr Thr Gln Glu Arg Ser His Ala Ile Gly Leu Gln Arg Lys
215                 220                 225

GGA CAG GAA TCT GCG CAG GAT CAC CCG GAT GGT GCT GGT GGT CGT GGC             1073
Gly Gln Glu Ser Ala Gln Asp His Pro Asp Gly Ala Gly Gly Arg Gly
230                 235                 240                 245

TGT ATT TAT CGT CTG CTG GAC CCC CAT CCA CAT CTA CGT CAT CAT CAA             1121
Cys Ile Tyr Arg Leu Leu Asp Pro His Pro His Leu Arg His His Gln
                250                 255                 260

AGC GCT GAT CAC GAT TCC AGA AAC CAC ATT TCA GAC CGT TTC CTG GCA             1169
Ser Ala Asp His Asp Ser Arg Asn His Ile Ser Asp Arg Phe Leu Ala
            265                 270                 275

CTT CTG CAT TGC TTT GGG TTA CAC GAA CAG CTG CCT GAA TCC AGT TCT             1217
Leu Leu His Cys Phe Gly Leu His Glu Gln Leu Pro Glu Ser Ser Ser
            280                 285                 290

TTA CGC CTT CCT GGA TGAAAACTTC AAGCGATGCT TCAGAGAGTT CTGCATCCCA             1272
Leu Arg Leu Pro Gly
    295

ACCTCGTCCA CGATCGAACA GCAAAACTCC ACTCGAGTCC GTCAGAACAC TAGGGAACAT          1332

CCCTCCACGG CTAATACAGT GGATCGAACT AACCACCAGC TAGAAAATCT GGAGGCAGAA          1392

ACTGCTCCAT TGCCCTAACT GGGTCTCACA CCATCCAGAC CCTCGCTAAG CTTAGAGGCC          1452

GCCATCTACG TGGAATCAGG TTGCTGTCAG GGTGTGTGGG AGGCTCTGGT TTCCTGAGAA          1512

ACCATCTGAT CCTGCATTCA AAGTCATTCC TCTCTGGCTA CTTCACTCTG CACATGAGAG          1572

ATGCTCAGAC TGATCAAGAC CAGAAGAAAG AAGAGACTAC CGGACA                        1618

(2) INFORMATION FOR SEQ ID NO:4:

(i) SEQUENCE CHARACTERISTICS:
        (A) LENGTH: 298 amino acids
        (B) TYPE: amino acid
        (D) TOPOLOGY: linear (ii) MOLECULE TYPE: protein
```

(xi) SEQUENCE DESCRIPTION: SEQ ID NO:4:

```
Met Arg Ser Glu Pro His Arg Ala Trp Arg Glu Arg Gln Pro Val Pro
 1               5                  10                  15

Ser Asp Arg Gln Pro Phe His Gly His Ser His Tyr His His Gly Pro
             20                  25                  30

Leu Leu Tyr Arg Val Cys Ser Gly Pro Leu Arg Lys Leu Pro Gly His
         35                  40                  45

Val Cys Asp Cys Lys Ile His Gln Asn Glu Asp Cys His Gln His Leu
     50                  55                  60

His Phe Gln Pro Cys Ser Gly Arg Arg Leu Ser Asp Gln Tyr Thr Ala
 65                  70                  75                  80

Leu Ser Glu Cys Gln Leu Pro Asp Gly Asn Met Ala Leu Arg Asn His
                 85                  90                  95

Pro Leu Gln Asp Arg Asp Leu Asn Arg Leu Leu Gln His Val His Gln
            100                 105                 110

His Ile His Pro Leu His His Glu Arg Gly Pro Leu His Cys Cys Leu
            115                 120                 125

Pro Pro Ser Gln Ser Pro Gly Phe Pro Tyr Pro Pro Lys Cys Gln Asn
130                 135                 140

Arg Gln Arg Leu Gln Leu Asp Pro Leu Phe Cys His Arg Ser Ala Cys
145                 150                 155                 160

Asn Val His Gly Asn His Lys Ile Gln Ala Gly Val His Arg Leu His
                165                 170                 175

Pro His Val Leu Pro Pro Asn Leu Val Leu Gly Glu Pro Ala Gln Asn
            180                 185                 190

Leu Cys Leu Tyr Leu Arg Phe His His Ala Asp Pro His His His Cys
            195                 200                 205

Val Leu Arg Pro Asp Asp Leu Thr Thr Gln Glu Arg Ser His Ala Ile
    210                 215                 220

Gly Leu Gln Arg Lys Gly Gln Glu Ser Ala Gln Asp His Pro Asp Gly
225                 230                 235                 240

Ala Gly Gly Arg Gly Cys Ile Tyr Arg Leu Leu Asp Pro His Pro His
                245                 250                 255

Leu Arg His His Gln Ser Ala Asp His Asp Ser Arg Asn His Ile Ser
            260                 265                 270

Asp Arg Phe Leu Ala Leu Leu His Cys Phe Gly Leu His Glu Gln Leu
            275                 280                 285

Pro Glu Ser Ser Ser Leu Arg Leu Pro Gly
290                 295
```

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:5:

ATCTTCACCC TCACCATGAT G                                              21

(2) INFORMATION FOR SEQ ID NO:6:

(i) SEQUENCE CHARACTERISTICS:
        (A) LENGTH: 20 base pairs
        (B) TYPE: nucleic acid (C) STRANDEDNESS: single
        (D) TOPOLOGY: linear (xi) SEQUENCE DESCRIPTION: SEQ ID NO:6:

CGGTCCTTCT CCTTGGAACC                                                    20

(2) INFORMATION FOR SEQ ID NO:7:

(i) SEQUENCE CHARACTERISTICS:
        (A) LENGTH: 372 amino acids
        (B) TYPE: amino acid
        (C) STRANDEDNESS:
        (D) TOPOLOGY: linear (xi) SEQUENCE DESCRIPTION: SEQ ID NO:7:

Met Glu Leu Val Pro Ser Ala Arg Ala Glu Leu Gln Ser Ser Pro Leu
1               5                  10                  15

Val Asn Leu Ser Asp Ala Phe Pro Ser Ala Phe Pro Ser Ala Gly Ala
            20                  25                  30

Asn Ala Leu Gly Ser Pro Gly Ala Arg Ser Ala Ser Met Leu Ala Leu
        35                  40                  45

Ala Ile Ala Ile Thr Ala Leu Tyr Ser Ala Val Cys Ala Val Gly Leu
    50                  55                  60

Leu Gly Asn Val Leu Val Met Phe Gly Ile Val Arg Tyr Thr Lys Leu
65                  70                  75                  80

Lys Thr Ala Thr Asn Ile Tyr Ile Phe Asn Leu Ala Leu Ala Asp Ala
                85                  90                  95

Leu Ala Thr Ser Thr Leu Pro Phe Gln Ser Val Asn Tyr Leu Met Glu
            100                 105                 110

Thr Trp Pro Phe Gly Glu Leu Leu Cys Lys Ala Val Leu Ser Ile Asp
        115                 120                 125

Tyr Tyr Asn Met Phe Thr Ser Ile Phe Thr Leu Thr Met Met Ser Val
    130                 135                 140

Asp Arg Tyr Ile Ala Val Cys His Pro Val Lys Ala Leu Asp Phe Arg
145                 150                 155                 160

Thr Pro Ala Lys Ala Lys Leu Ile Asn Ile Cys Ile Trp Val Leu Ala
                165                 170                 175

Ser Gly Val Gly Val Pro Ile Met Val Met Ala Val Thr Gln Pro Arg
            180                 185                 190

Asp Gly Ala Val Val Cys Met Leu Gln Phe Pro Ser Pro Ser Trp Tyr
        195                 200                 205

Trp Asp Thr Val Thr Lys Ile Cys Val Phe Ile Phe Ala Phe Val Val
    210                 215                 220

Pro Ile Leu Ile Ile Thr Val Cys Tyr Gly Leu Met Leu Leu Arg Leu
225                 230                 235                 240

Arg Ser Val Arg Leu Leu Ser Gly Ser Lys Glu Lys Asp Arg Ser Leu
                245                 250                 255

Arg Arg Ile Thr Arg Met Val Leu Val Val Gly Ala Phe Val Val
            260                 265                 270

Cys Trp Ala Pro Ile His Ile Phe Val Ile Val Trp Thr Leu Val Asp
        275                 280                 285

Ile Asn Arg Arg Asp Pro Leu Val Val Ala Ala Leu His Leu Cys Ile
    290                 295                 300

Ala Leu Gly Tyr Ala Asn Ser Ser Leu Asn Pro Val Leu Tyr Ala Phe
305                 310                 315                 320

Leu Asp Glu Asn Phe Lys Arg Cys Phe Arg Gln Leu Cys Arg Thr Pro

```
                    325                 330                 335
Cys Gly Arg Gln Glu Pro Gly Ser Leu Arg Arg Pro Arg Gln Ala Thr
                340                 345                 350

Thr Arg Glu Arg Val Thr Ala Cys Thr Pro Ser Asp Gly Pro Gly Gly
                355                 360                 365

Gly Ala Ala Ala
            370

(2) INFORMATION FOR SEQ ID NO:8:

(i) SEQUENCE CHARACTERISTICS:
        (A) LENGTH: 391 amino acids
        (B) TYPE: amino acid
        (C) STRANDEDNESS:
        (D) TOPOLOGY: linear (xi) SEQUENCE DESCRIPTION: SEQ ID NO:8:

Met Phe Pro Asn Gly Thr Ala Pro Ser Pro Thr Ser Ser Pro Ser Ser
 1               5                  10                  15

Ser Pro Gly Gly Cys Gly Glu Gly Leu Cys Ser Arg Gly Pro Gly Ser
                20                  25                  30

Gly Ala Ala Asp Gly Met Glu Glu Pro Gly Arg Asn Leu Ser Gln Asn
            35                  40                  45

Gly Thr Leu Ser Glu Gly Gln Gly Ser Ala Ile Leu Ile Ser Phe Ile
     50                  55                  60

Tyr Ser Val Val Cys Leu Val Gly Leu Cys Gly Asn Ser Met Val Ile
65                  70                  75                  80

Tyr Val Ile Leu Arg Tyr Ala Lys Met Lys Thr Ala Thr Asn Ile Tyr
                85                  90                  95

Ile Leu Asn Leu Ala Ile Ala Asp Glu Leu Leu Met Leu Ser Val Pro
                100                 105                 110

Phe Leu Val Thr Ser Thr Leu Leu Arg His Trp Pro Phe Gly Ala Leu
            115                 120                 125

Leu Cys Arg Leu Val Leu Ser Val Asp Ala Tyr Asn Met Phe Thr Ser
    130                 135                 140

Ile Tyr Cys Leu Thr Val Leu Ser Val Asp Arg Tyr Val Ala Val Val
145                 150                 155                 160

His Pro Ile Lys Ala Ala Arg Tyr Arg Arg Pro Thr Val Ala Lys Val
                165                 170                 175

Val Asn Leu Gly Val Trp Val Leu Ser Leu Leu Val Ile Leu Pro Ile
                180                 185                 190

Val Val Phe Ser Arg Thr Ala Ala Asn Ser Asp Gly Thr Val Ala Cys
            195                 200                 205

Asn Met Leu Met Pro Glu Pro Ala Gln Arg Trp Leu Val Gly Phe Val
    210                 215                 220

Leu Tyr Thr Phe Leu Met Gly Phe Leu Leu Pro Val Gly Ala Ile Cys
225                 230                 235                 240

Leu Cys Tyr Val Leu Ile Ile Ala Lys Met Arg Met Val Ala Leu Lys
                245                 250                 255

Ala Gly Trp Gln Gln Arg Lys Arg Ser Glu Arg Lys Ile Thr Leu Met
            260                 265                 270

Val Met Met Val Val Met Val Phe Val Ile Cys Trp Met Pro Phe Tyr
    275                 280                 285

Val Val Gln Leu Val Asn Val Phe Ala Glu Gln Asp Asp Ala Thr Val
    290                 295                 300
```

```
Ser Gln Leu Ser Val Ile Leu Gly Tyr Ala Asn Ser Cys Ala Asn Pro
305                 310                 315                 320

Ile Leu Tyr Gly Phe Leu Ser Asp Asn Phe Lys Arg Ser Phe Gln Arg
                325                 330                 335

Ile Leu Cys Leu Ser Trp Met Asp Asn Ala Ala Glu Glu Pro Val Asp
                340                 345                 350

Tyr Tyr Ala Thr Ala Leu Lys Ser Arg Ala Tyr Ser Val Glu Asp Phe
                355                 360                 365

Gln Pro Glu Asn Leu Glu Ser Gly Gly Val Phe Arg Asn Gly Thr Cys
370                 375                 380

Ala Ser Arg Ile Ser Thr Leu
385                 390

(2) INFORMATION FOR SEQ ID NO:9:

(i) SEQUENCE CHARACTERISTICS:
        (A) LENGTH: 369 amino acids
        (B) TYPE: amino acid
        (C) STRANDEDNESS:
        (D) TOPOLOGY: linear (xi) SEQUENCE DESCRIPTION: SEQ ID NO:9:

Met Glu Leu Thr Ser Glu Gln Phe Asn Gly Ser Gln Val Trp Ile Pro
1               5                   10                  15

Ser Pro Phe Asp Leu Asn Gly Ser Leu Gly Pro Ser Asn Gly Ser Asn
                20                  25                  30

Gln Thr Glu Pro Tyr Tyr Asp Met Thr Ser Asn Ala Val Leu Thr Phe
            35                  40                  45

Ile Tyr Phe Val Val Cys Val Val Gly Leu Cys Gly Asn Thr Leu Val
        50                  55                  60

Ile Tyr Val Ile Leu Arg Tyr Ala Lys Met Lys Thr Ile Thr Asn Ile
65                  70                  75                  80

Tyr Ile Leu Asn Leu Ala Ile Ala Asp Glu Leu Phe Met Leu Gly Leu
                85                  90                  95

Pro Phe Leu Ala Met Gln Val Ala Leu Val His Trp Pro Phe Gly Lys
                100                 105                 110

Ala Ile Cys Arg Val Val Met Thr Val Asp Gly Ile Asn Gln Phe Thr
            115                 120                 125

Ser Ile Phe Cys Leu Thr Val Met Ser Ile Asp Arg Tyr Leu Ala Val
130                 135                 140

Val His Pro Ile Lys Ser Ala Lys Trp Arg Arg Pro Arg Thr Ala Lys
145                 150                 155                 160

Met Ile Asn Val Ala Val Trp Gly Val Ser Leu Leu Val Ile Leu Pro
                165                 170                 175

Ile Met Ile Tyr Ala Gly Leu Arg Ser Asn Gln Trp Gly Arg Ser Ser
                180                 185                 190

Cys Thr Ile Asn Trp Pro Gly Glu Ser Gly Ala Trp Tyr Thr Gly Phe
            195                 200                 205

Ile Ile Tyr Ala Phe Ile Leu Gly Phe Leu Val Pro Leu Thr Ile Ile
        210                 215                 220

Cys Leu Cys Tyr Leu Arg Ile Ile Lys Val Lys Ser Ser Gly Ile
225                 230                 235                 240

Arg Val Gly Ser Ser Lys Arg Lys Lys Ser Glu Lys Lys Val Thr Arg
                245                 250                 255

Met Val Ser Ile Val Val Ala Val Phe Ile Phe Cys Trp Leu Pro Phe
                260                 265                 270
```

―continued

```
Tyr Ile Phe Asn Val Ser Ser Val Ser Val Ala Ile Ser Pro Thr Pro
        275                 280                 285
Ala Leu Lys Gly Met Phe Asp Phe Val Val Ile Leu Thr Tyr Ala Asn
        290                 295                 300
Ser Cys Ala Asn Pro Ile Leu Tyr Ala Phe Leu Ser Asp Asn Phe Lys
305                 310                 315                 320
Lys Ser Phe Gln Asn Val Leu Cys Leu Val Lys Val Ser Gly Ala Glu
                325                 330                 335
Asp Gly Glu Arg Ser Asp Ser Lys Gln Asp Lys Ser Arg Leu Asn Glu
                340                 345                 350
Thr Thr Glu Thr Gln Arg Thr Leu Leu Asn Gly Asp Leu Gln Thr Ser
        355                 360                 365
Ile
```